US008486669B2

(12) United States Patent
Balensiefer et al.

(10) Patent No.: US 8,486,669 B2
(45) Date of Patent: Jul. 16, 2013

(54) ENZYMATIC HYDROLYSIS OF A CELLULOSE MATERIAL TREATED WITH AN IONIC LIQUID

(75) Inventors: Tim Balensiefer, Mannheim (DE); Julia Brodersen, Mannheim (DE); Giovanni D'Andola, Heidelberg (DE); Klemens Massonne, Bad Duerkheim (DE); Stephan Freyer, Neustadt (DE); Veit Stegmann, Mannheim (DE)

(73) Assignee: BASF SE, Ludwigshafen (DE)

( * ) Notice: Subject to any disclaimer, the term of this patent is extended or adjusted under 35 U.S.C. 154(b) by 569 days.

(21) Appl. No.: 12/523,327

(22) PCT Filed: Jan. 22, 2008

(86) PCT No.: PCT/EP2008/050709
§ 371 (c)(1),
(2), (4) Date: Jul. 16, 2009

(87) PCT Pub. No.: WO2008/090155
PCT Pub. Date: Jul. 31, 2008

(65) Prior Publication Data
US 2010/0112646 A1    May 6, 2010

(30) Foreign Application Priority Data
Jan. 23, 2007    (EP) .................................... 07101034

(51) Int. Cl.
*C12P 19/02*    (2006.01)
(52) U.S. Cl.
USPC ........................................................ 435/105
(58) Field of Classification Search
USPC ........................................................ 435/105
See application file for complete search history.

(56) References Cited

U.S. PATENT DOCUMENTS

| 2004/0096932 A1 | 5/2004 | Kragl et al. |
| 2008/0164440 A1 | 7/2008 | Maase et al. |
| 2008/0190321 A1 | 8/2008 | Maase et al. |
| 2008/0254515 A1 | 10/2008 | Boy et al. |
| 2008/0269477 A1 | 10/2008 | Stegmann et al. |
| 2008/0287684 A1 | 11/2008 | Exner et al. |
| 2008/0299606 A1 | 12/2008 | Pompejus et al. |
| 2008/0318287 A1 | 12/2008 | Boy et al. |
| 2009/0020112 A1 | 1/2009 | Massonne et al. |
| 2009/0062524 A1 | 3/2009 | Massonne et al. |
| 2009/0182138 A1 | 7/2009 | Massonne et al. |
| 2009/0187016 A1 | 7/2009 | Massone et al. |
| 2009/0226571 A1 | 9/2009 | Freyer et al. |
| 2009/0281303 A1 | 11/2009 | Massonne et al. |
| 2009/0326216 A1 | 12/2009 | Stegmann et al. |

FOREIGN PATENT DOCUMENTS

| DE | 10 2005 017 715 | 10/2006 |
| DE | 10 2005 017 733 | 10/2006 |
| EP | 1 332 221 | 8/2003 |
| WO | 03 029329 | 4/2003 |
| WO | 2004 084627 | 10/2004 |
| WO | 2005 017001 | 2/2005 |
| WO | 2005 017252 | 2/2005 |
| WO | 2006 108861 | 10/2006 |
| WO | WO 2006/136529 A1 | 12/2006 |
| WO | WO 2007/101813 A1 | 9/2007 |
| WO | 2008 098036 | 8/2008 |
| WO | 2008 112291 | 9/2008 |

OTHER PUBLICATIONS

U.S. Appl. No. 12/747,372, filed Jun. 10, 2010, Degen, et al.
U.S. Appl. No. 12/445,081, filed Apr. 10, 2009, D'Andola, et al.
U.S. Appl. No. 12/598,934, filed Nov. 5, 2009, Tishkov, et al.
Dadi, A.P. et al., "Enhancement of Cellulose Saccharification Kinetics Using an Ionic Liquid Pretreatment Step", Biotechnology and Bioengineering, vol. 95, No. 5, pp. 904-910 (Dec. 5, 2006) XP-002470828.
Kilpelaeinen, I. et al., "Dissolution of Wood in Ionic Liquids", Journal of Agricultural and Food Chemistry, vol. 55, No. 22, pp. 9142-9148 (Oct. 31, 2007) XP-002470829.
Galbe, M. et al., "A Review of the Production of Ethanol From Softwood", App. Microbiol Biotechnol, vol. 59, pp. 618-628 (2002).
Zhu, S. et al., "Dissolution of Cellulose With Ionic Liquids and Its Application: A Mini-Review", Green Chem., vol. 8, pp. 325-327 (2006).
Fort, D. A. et al., "Can Ionic Liquids Dissolve Wood? Processing and Analysis of Lignocellulosic Materials With 1-n-Butyl-3-Methylimidazolium Chloride", Green Chem., vol. 9, pp. 63-69 (2007).
Liying, L. et al., "Enzymatic Hydrolysis of Cellulose Materials Treated With Ionic Liquid [BMIM] Cl", Chinese Science Bulletin, vol. 51, No. 21, pp. 2432-2436 (Oct. 2006).
U.S. Appl. No. 12/523,740, filed Jul. 20, 2009, Balensiefer, et al.
U.S. Appl. No. 12/811,100, filed Jun. 29, 2010, Beste, et al.

*Primary Examiner* — Suzanne M Noakes
*Assistant Examiner* — Stephen Chong
(74) *Attorney, Agent, or Firm* — Oblon, Spivak, McClelland, Maier & Neustadt, L.L.P.

(57) ABSTRACT

A process for preparing glucose from a cellulose material, in which a cellulose-comprising starting material is provided and treated with a liquid treatment medium comprising an ionic liquid whose anions are selected from among polyatomic anions and the cellulose-comprising material which has been treated with the ionic liquid is subjected to an enzymatic hydrolysis, is described.

40 Claims, 3 Drawing Sheets

ENZYMATIC HYDROLYSIS OF A CELLULOSE MATERIAL TREATED WITH AN IONIC LIQUID

CROSS-REFERENCE TO RELATED APPLICATIONS

Figure 1:
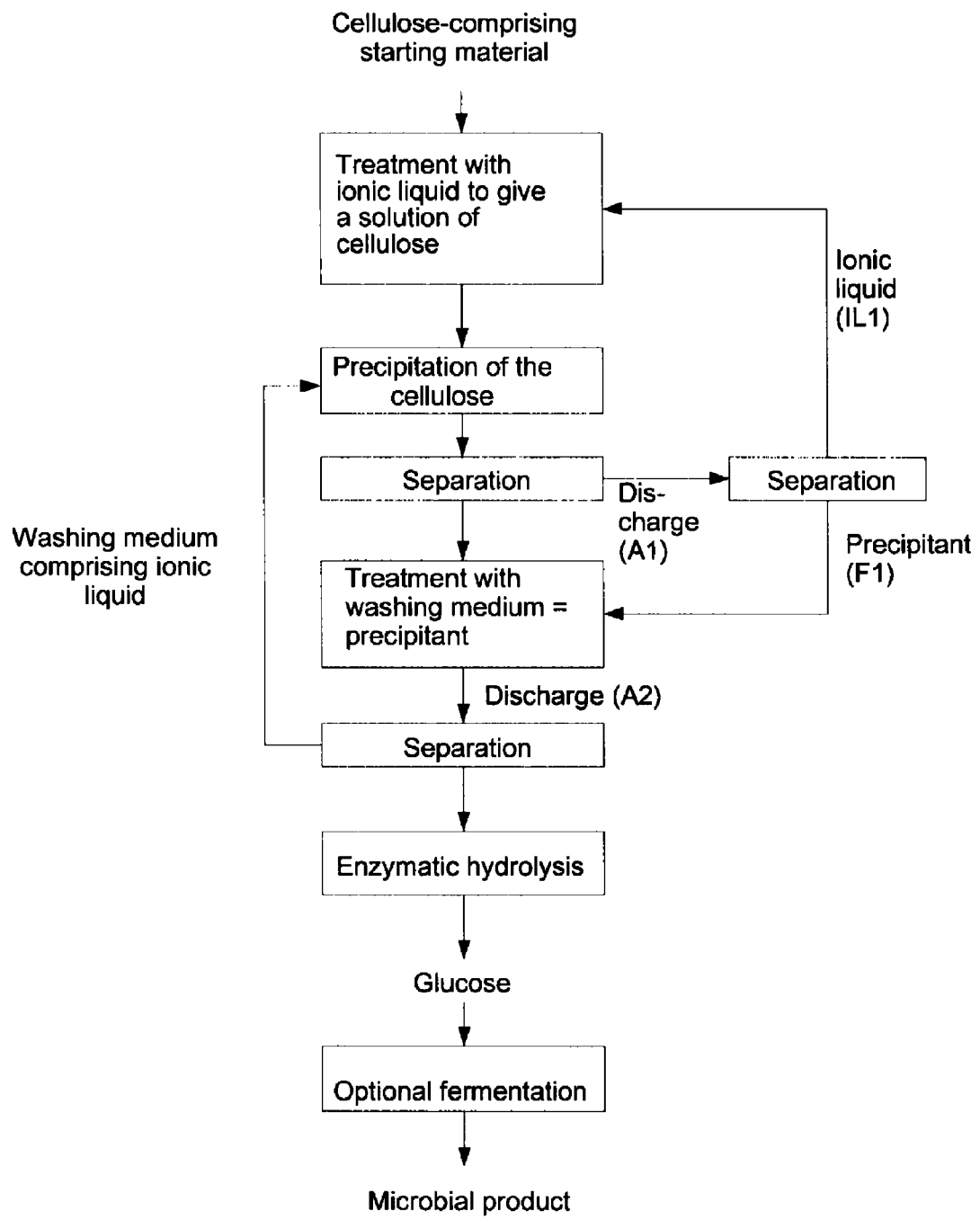

This application is a 371 of PCT/EP08/05709 filed Jan. 22, 2008 and claims the benefit of EP 07101034.2 filed The present invention relates to a process for preparing glucose from a cellulose-comprising starting material, in which this is firstly treated with an ionic liquid and subsequently subjected to an enzymatic hydrolysis. The invention further relates to a process for preparing microbial material transformation products, especially ethanol, by additionally subjecting the glucose obtained to a fermentation.

With a proportion of about 700 billion metric tons of the estimated biomass stock of 1.5 trillion metric tons on earth, cellulose is the most important representative of the group of organic biopolymers and a very versatile raw material. In the textile industry, cellulose is, for example, the most important constituent of fiber raw materials, in particular of cotton. Pulp obtained from wood and cotton, which comprises a very high proportion of cellulose, is at present the most important raw material base for the production of paper, board, reconstituted cellulose fibers and films. Hydrolysis of cellulose to glucose will in future be of particular importance, since this could, for example, open up a route to large amounts of bioethanol obtained by fermentation.

In Appl. Microbiol. Biotechnol., 2002, 59, pp. 618-628, M. Galbe and G. Zacchi give an overview of the preparation of ethanol from lignocellulose sources. The conversion of lignocellulose into sugars and further into ethanol is associated with various problems. All known preparative processes comprise, as common step, the hydrolysis of cellulose and, if appropriate, hemicellulose to the monomeric sugars. This hydrolysis can be carried out using concentrated acids, dilute acids or enzymatically. Relatively old conventional digestion methods for lignocellulose use aqueous reaction systems and drastic reaction conditions such as high temperatures, high pressures and the use of Brönsted acids. As a result of corrosion problems, large quantities of by-products and the high plant costs, these processes are not pursued to a significant extent at present. As an alternative, the cellulose-comprising material can be subjected to a pretreatment to make the cellulose accessible to enzymatic hydrolysis. Thus, for example, the process of "Steam Explosion" employs high pressures in the presence or absence of acidic catalysts in order to break up the microcrystalline structure of the cellulose and thus make efficient enzymatic hydrolysis possible. The use of gaseous $SO_2$ or of very dilute aqueous sulfuric acid can counter the corrosion problems, but the process then instead has other disadvantages. Thus, $SO_2$ is highly toxic and the large material streams associated with the use of very dilute $H_2SO_4$ lead to economic disadvantages. In addition, this form of pretreatment leads to long reaction times in the subsequent enzymatic hydrolysis at moderate enzyme activity and gives only moderate yields of glucose. There is therefore a continuing need for an effective process for preparing glucose from cellulose materials and especially a suitable pretreatment which makes rapid and very complete enzymatic degradation of cellulose possible.

It is known that various ionic liquids can be used as solvents for cellulose. Thus, S. Zhu et al. in Green Chem. 2006, 8, pp. 325-327, describe in quite general terms the possibility of dissolving cellulose in ionic liquids and recovering it by addition of suitable precipitates such as water, ethanol or acetone. As suitable ionic liquids, specific mention is made of 1-butyl-3-methylimidazolium chloride (BMIMCl) and 1-allyl-3-methylimidazolium chloride (AMIMCl).

EP-A-1 332 221 describes an enzymatic catalysis in the presence of ionic liquids.

WO 03/029329 teaches the dissolution of cellulose in an ionic liquid which must comprise essentially no water and no nitrogen-comprising bases for further processing of the cellulose.

WO 2004/084627 describes a process for producing capsules composed of regenerated cellulose with an active substance present therein, in which an ionic liquid is used as solvent.

WO 2005/017001 describes a process for dissolving a lignocellulose material by means of an ionic liquid with microwave irradiation and/or under pressure and in the absence of water. The cations of the ionic liquid correspond to those mentioned in WO 2004/084627.

WO 2005/017252 describes a process for the treatment of a lignocellulose material with an ionic liquid, e.g. for delignification.

DE 102005017733 describes solutions comprising cellulose, an ionic liquid as solvent and from 6 to 30% by weight of a nitrogen-comprising base, based on the total weight of the solution.

DE 10 2005 017 715 describes solutions comprising cellulose and an ionic liquid based on cations having at least one atom which is selected from among nitrogen, oxygen, sulfur and phosphorus and is present in protonated form.

In a poster presentation at the 28th Symposium on Biotechnology for Fuels and Chemicals, Poster 2-61, Nashville, Tenn., USA, Apr. 30-May 3, 2006, and in Biotechnology and Bioengineering, Vol. 95, No. 5, 2006, pp. 904-910 (published online on Aug. 17, 2006), A. P. Dadi, S. Varanasi and C. A. Schall describe the pretreatment of cellulose with 1-butyl-3-methylimidazolium chloride (BMIMCl) before the enzymatically catalyzed hydrolysis to glucose. Here, the particular role of the chloride anion in the desired structural alteration of the cellulose is emphasized. The small size of the anion, the high electronegativity and the high basicity are said to lead to particularly good attack on the free hydroxyl groups of the cellulose and thus bring about the break-up of the crystalline structure. Nevertheless, this pretreatment method is still capable of improvement in a number of respects. Thus, the pretreatment of the cellulose is carried out under anhydrous conditions, which, inter alia, makes it necessary to work under a nitrogen atmosphere in order to avoid absorption of water. The additional expense associated with working in the absence of water is a significant disadvantage of this process. In addition, the chloride anion is highly corrosive. The rate of the enzymatic liberation of glucose, especially at the beginning of the reaction, is also capable of improvement.

It has now surprisingly been found that ionic liquids based on polyatomic (multiatomic) anions are particularly advantageous for the pretreatment of cellulose materials for enzymatic hydrolysis to glucose.

The invention accordingly provides a process for preparing glucose from a cellulose material, wherein a cellulose-comprising starting material is provided and is treated with a liquid treatment medium comprising an ionic liquid whose anions are selected from among polyatomic anions and the cellulose-comprising material which has been treated with the ionic liquid is subjected to an enzymatic hydrolysis.

In its embodiments described below, the process of the invention is advantageous in respect of one or more of the following points:

tolerance toward water; the ionic liquids based on polyatomic anions which are used according to the invention generally tolerate the presence of water in an amount at which precipitation of the cellulose from the treatment medium does not yet occur;

it is not necessary to work under protective gas;

more rapid enzymatic reaction of the pretreated cellulose;

lower amounts of enzyme based on substrate used;

possibility of higher substrate concentrations in the enzymatic hydrolysis;

the corrosion problems associated with the use of monoatomic anions, especially Cl, do not occur.

A significant advantage of the process of the invention is the possibility of carrying out the treatment of the cellulose-comprising starting material in the presence of water. The water content of the liquid treatment medium can be up to about 15% by weight. Naturally, the liquid treatment medium can also consist entirely of at least one ionic liquid.

Cellulose is a generally highly crystalline biopolymer of D-anhydroglucopyranose having long chains of sugar units linked by β-1,4-glycosidic bonds. The individual polymer chains are joined to one another by intermolecular and intramolecular hydrogen bonds and van der Waals interactions. The treatment according to the invention of the cellulose with an ionic liquid leads to improved enzymatic hydrolysis of the resulting (regenerated) cellulose. It is assumed that the treatment increases the number of points at which the enzymes can bind to the polymer chain. This is generally associated with a reduction in the proportion of crystalline material and a corresponding increase in the proportion of amorphous material, as can be established, for example, by means of XRD.

Preferred cellulose-comprising starting materials for the process of the invention are cellulose, cellulose-comprising paper materials and cellulose-rich natural fiber materials such as flax, hemp, sisal, jute, straw, coconut fibers, switchgrass (*Panicum virgatum*) and other natural fibers. It goes without saying that the cellulose used is a cellulose which can still undergo a structural change in the above-described sense, i.e. is an unpretreated cellulose or a pretreated cellulose which still has appropriately high proportions of crystalline material.

The glucose obtained by the process of the invention can still comprise small amounts of oligosaccharides (celluoligosaccharides). The proportion of oligosaccharides is preferably not more than 15% by weight, particularly preferably not more than 10% by weight, based on the total weight of the product obtained in the enzymatic hydrolysis. A proportion of oligosaccharides is generally not critical for a subsequent fermentation of the glucose.

For the purposes of the present patent application, ionic liquids are organic salts which are liquid at temperatures below 180° C. The ionic liquids preferably have a melting point of less than 180° C. Furthermore, the melting point is preferably in a range from −50° C. to 150° C., more preferably in the range from −20° C. to 120° C. and even more preferably below 100° C.

Ionic liquids which are in the liquid state of matter at room temperature are described, for example, by K. N. Marsh et al., Fluid Phase Equilibria 219 (2004), 93-98 and J. G. Huddleston et al., Green Chemistry 2001, 3, 156-164.

Cations and anions are present in the ionic liquid. In the ionic liquid, a proton or an alkyl radical can be transferred from the cation to the anion, resulting in two uncharged molecules. An equilibrium between anions, cations and uncharged molecules formed therefrom can thus be present in the ionic liquid used according to the invention.

The ionic liquids used according to the invention have polyatomic, i.e. multiatomic, anions having two or more than two atoms.

For the purposes of the present invention, the expression "alkyl" comprises straight-chain or branched alkyl. This is preferably straight-chain or branched $C_1$-$C_{30}$-alkyl, in particular $C_1$-$C_{18}$-alkyl and very particularly preferably $C_1$-$C_{12}$-alkyl. Examples of alkyl groups are, in particular, methyl, ethyl, n-propyl, isopropyl, n-butyl, isobutyl, sec-butyl, tert-butyl, n-pentyl, isopentyl, 1-methylbutyl, tert-pentyl, neopentyl, n-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, n-heptyl, n-octyl, 1-methylheptyl, 2-ethylhexyl, 2,4,4-trimethyl-pentyl, 1,1,3,3-tetramethylbutyl, n-nonyl, n-decyl, n-undecyl, n-dodecyl, n-tridecyl, n-tetradecyl, n-pentadecyl, n-hexadecyl, n-heptadecyl, n-octadecyl and n-eicosyl.

The expression alkyl also comprises alkyl radicals whose carbon chain may be interrupted by one or more nonadjacent heteroatoms or heteroatom-comprising groups which are preferably selected from among —O—, —S—, —NR$^a$—, —PR$^a$—, —SiR$^a$R$^{aa}$ and/or —SO$_2$. R$^a$ is preferably hydrogen, alkyl, cycloalkyl, heterocycloalkyl, aryl or hetaryl. R$^{aa}$ is preferably hydrogen, alkyl, cycloalkyl, heterocycloalkyl or aryl.

Examples of alkyl radicals whose carbon chains may be interrupted by one or two nonadjacent heteroatoms —O— are the following:

methoxymethyl, diethoxymethyl, 2-methoxyethyl, 2-ethoxyethyl, 2-propoxyethyl, diethoxyethyl, 2-butoxyethyl, 2-octyloxyethyl, 2-methoxypropyl, 3-methoxypropyl, 3-ethoxypropyl, 3-propoxypropyl, 2-isopropoxyethyl, 2-butoxypropyl, 3-butoxypropyl, 4-methoxybutyl, 4-ethoxybutyl, 4-propoxybutyl, 6-methoxyhexyl, 3,6-dioxaheptyl (5-methoxy-3-oxapentyl), 3,6-dioxaoctyl (7-methoxy-4-oxaheptyl), 4,8-dioxanonyl (7-methoxy-4-oxaheptyl), 3,7-dioxaoctyl, 3,7-dioxanonyl, 4,7-dioxaoctyl, 4,7-dioxanonyl, 2- and 4-butoxybutyl, 4,8-dioxadecyl, 9-ethoxy-5-oxanonyl.

Examples of alkyl radicals whose carbon chains may be interrupted by three or more than three nonadjacent heteroatoms —O— also include oligooxyalkylenes and polyoxyalkylenes, i.e. compounds having repeating units which are preferably selected from among $(CH_2CH_2O)_{x1}$, $(CH(CH_3)CH_2O)_{x2}$ and $((CH_2)_4O)_{x3}$, where ×1, ×2 and ×3 are each, independently of one another, an integer from 3 to 100, preferably from 3 to 80. The sum of ×1, ×2 and ×3 is an integer from 3 to 300, in particular from 3 to 100. In polyoxyalkylenes having two or three different repeating units, the repeating units can be present in any order, i.e. they can be randomly distributed, alternating or block-like repeating units. Examples are 3,6,9-trioxadecyl, 3,6,9-trioxaundecyl, 3,6,9-trioxa-dodecyl, 4,8,12-trioxamidecyl (11-methoxy-4,8-dioxaundecyl), 4,8,12-trioxatetradecyl, 14-methoxy-5,10-dioxatetradecyl, 5,10,15-trioxaheptadecyl, 3,6,9,12-tetraoxamidecyl, 3,6,9,12-tetraoxatetradecyl, 4,8,12,16-tetraoxaheptadecyl (15-methoxy-4,8,12-trioxa-pentadecyl), 4,8,12,16-tetraoxaoctadecyl and the like.

Examples of alkyl radicals whose carbon chains may be interrupted by one or more, e.g. 1, 2, 3, 4 or more than 4, nonadjacent heteroatoms —S— are the following:

butylthiomethyl, 2-methylthioethyl, 2-ethylthioethyl, 2-propylthioethyl, 2-butylthioethyl, 2-dodecylthioethyl, 3-methylthiopropyl, 3-ethylthiopropyl, 3-propylthiopropyl, 3-butylthiopropyl, 4-methylthiobutyl, 4-ethylthiobutyl, 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiamidecyl and 3,6,9,12-tetrathiatetradecyl.

Examples of alkyl radicals whose carbon chains are interrupted by one or two nonadjacent heteroatom-comprising groups —$NR^a$— are the following:

2-monomethylaminoethyl and 2-monoethylaminoethyl, 2-dimethylaminoethyl, 3-methylaminopropyl, 2- and 3-dimethylaminopropyl, 3-monoisopropylaminopropyl, 2- and 4-monopropylaminobutyl, 2- and 4-dimethylaminobutyl, 6-methylaminohexyl, 6-dimethylaminohexyl, 6-methyl-3,6-diazaheptyl, 3,6-dimethyl-3,6-diazaheptyl, 3,6-diazaoctyl and 3,6-dimethyl-3,6-diazaoctyl.

Examples of alkyl radicals whose carbon chains may be interrupted by three or more than three nonadjacent heteroatom-comprising groups —$NR^a$— also include oligoalkylenimines and polyalkylenimines. What has been said above with regard to the polyoxyalkylenes applies analogously to polyalkylenimines, with the oxygen atom being in each case replaced by an $NR^a$ group, where $R^a$ is preferably hydrogen or $C_1$-$C_4$-alkyl. Examples are 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetra-azamidecyl, 3,6,9,12-tetramethyl-3,6,9,12-tetraazamidecyl and the like.

Examples of alkyl radicals whose carbon chains are interrupted by one or more, e.g. 1 or 2, nonadjacent —$SO_2$— groups are 2-methylsulfonylethyl, 2-ethylsulfonylethyl, 2-propylsulfonylethyl, 2-isopropylsulfonylethyl, 2-butylsulfonylethyl, 2-methyl-sulfonylpropyl, 3-methylsulfonylpropyl, 2-ethylsulfonylpropyl, 3-ethylsulfonylpropyl, 2-propylsulfonylpropyl, 3-propylsulfonylpropyl, 2-butylsulfonylpropyl, 3-butylsulfonyl-propyl, 2-methylsulfonylbutyl, 4-methylsulfonylbutyl, 2-ethylsulfonylbutyl, 4-ethyl-sulfonylbutyl, 2-propylsulfonylbutyl, 4-propylsulfonylbutyl and 4-butylsulfonylbutyl.

The expression alkyl also comprises substituted alkyl radicals. Substituted alkyl groups can, depending on the length of the alkyl chain, have one or more (e.g. 1, 2, 3, 4, 5 or more than 5) substituents. These are preferably selected independently from among cycloalkyl, cycloalkyloxy, polycyclyl, polycyclyloxy, heterocycloalkyl, aryl, aryloxy, arylthio, hetaryl, halogen, hydroxy, SH, =O, =S, =$NR^a$, COON, carboxylate, $SO_3H$, sulfonate, $NE^1E^2$, nitro and cyano, where $E^1$ and $E^2$ are each, independently of one another, hydrogen, alkyl, cycloalkyl, heterocycloalkyl, aryl or hetaryl. Cycloalkyl, cycloalkyloxy, polycycloalkyl, polycycloalkyloxy, heterocycloalkyl, aryl and hetaryl substituents of the alkyl groups may in turn be unsubstituted or substituted; suitable substituents are those mentioned below for these groups.

What has been said above with regard to alkyl also applies in principle to the alkyl parts of alkoxy, alkylamino, dialkylamino, alkylthio (alkylsulfanyl), alkylsulfinyl, alkylsulfonyl, etc.

Suitable substituted alkyl radicals are the following:

alkyl substituted by carboxy, e.g. carboxymethyl, 2-carboxyethyl, 3-carboxypropyl, 4-carboxybutyl, 5-carboxypentyl, 6-carboxyhexyl, 7-carboxyheptyl, 8-carboxyoctyl, 9-carboxynonyl, 10-carboxydecyl, 12-carboxydodecyl and 14-carboxytetradecyl;

alkyl substituted by $SO_3H$, e.g. sulfomethyl, 2-sulfoethyl, 3-sulfopropyl, 4-sulfobutyl, 5-sulfopentyl, 6-sulfohexyl, 7-sulfoheptyl, 8-sulfooctyl, 9-sulfononyl, 10-sulfodecyl, 12-sulfododecyl and 14-sulfotetradecyl;

alkyl substituted by carboxylate, for example alkoxycarbonylalkyl, e.g. methoxy-carbonylmethyl, ethoxycarbonylmethyl, n-butoxycarbonylmethyl, 2-methoxycarbonyl-ethyl, 2-ethoxycarbonylethyl, 2-methoxycarbonylpropyl, 2-ethoxycarbonylpropyl, 2-(n-butoxycarbonyl)propyl, 2-(4-n-butoxycarbonyl)propyl, 3-methoxycarbonylpropyl, 3-ethoxycarbonylpropyl, 3-(n-butoxycarbonyl)propyl, 3-(4-n-butoxycarbonyl)propyl, aminocarbonylalkyl, e.g. aminocarbonylmethyl, aminocarbonylethyl, aminocarbonylpropyl and the like; alkylaminocarbonylalkyl such as methylaminocarbonylmethyl, methylaminocarbonylethyl, ethylcarbonylmethyl, ethylcarbonylethyl and the like, or dialkylaminocarbonylalkyl such as dimethylaminocarbonylmethyl, dimethylamino-carbonylethyl, dimethylcarbonylpropyl, diethylaminocarbonylmethyl, diethylamino-carbonylethyl, diethylcarbonylpropyl and the like;

alkyl substituted by hydroxy, e.g. 2-hydroxyethyl, 2-hydroxypropyl, 3-hydroxypropyl, 3-hydroxybutyl, 4-hydroxybutyl, 2-hydroxy-2,2-dimethylethyl, 5-hydroxy-3-oxapentyl, 6-hydroxyhexyl, 7-hydroxy-4-oxaheptyl, 8-hydroxy-4-oxaoctyl, 8-hydroxy-3,6-dioxaoctyl, 9-hydroxy-5-oxanonyl, 11-hydroxy-4,8-dioxaundecyl, 11-hydroxy-3,6,9-trioxaundecyl, 14-hydroxy-5,10-dioxatetradecyl, 15-hydroxy-4,8,12-trioxapentadecyl and the like;

alkyl substituted by amino, e.g. 2-aminoethyl, 2-aminopropyl, 3-aminopropyl, 4-amino-butyl, 6-aminohexyl and the like;

alkyl substituted by cyano, e.g. 2-cyanoethyl, 3-cyanopropyl, 3-cyanobutyl and 4-cyanobutyl;

alkyl substituted by halogen as defined below, where the hydrogen atoms in the alkyl group may be partly or completely replaced by halogen atoms, e.g. $C_1$-$C_{18}$-fluoroalkyl, e.g. trifluoromethyl, difluoromethyl, fluoromethyl, pentafluoroethyl, heptafluoropropyl, heptafluoroisopropyl, nonafluorobutyl, nonafluoroisobutyl, undecylfluoropentyl, undecylfluoroisopentyl and the like, $C_1$-$C_{18}$-chloroalkyl, e.g. chloromethyl, dichloromethyl, trichloromethyl, 2-chloroethyl, 2- and 3-chloropropyl, 2-, 3- and 4-chlorobutyl, 1,1-dimethyl-2-chloroethyl and the like, $C_1$-$C_{18}$-bromoalkyl, e.g. bromoethyl, 2-bromoethyl, 2- and 3-bromopropyl and 2-, 3- and 4-bromobutyl and the like;

alkyl substituted by nitro, e.g. 2-nitroethyl, 2- and 3-nitropropyl and 2-, 3- and 4-nitro-butyl and the like;

alkyl substituted by cycloalkyl, e.g. cyclopentylmethyl, 2-cyclopentylethyl, 3-cyclo-pentylpropyl, cyclohexylmethyl, 2-cyclohexylethyl, 3-cyclohexylpropyl and the like;

alkyl substituted by =O (oxo group), e.g. 2-oxopropyl, 2-oxobutyl, 3-oxobutyl, 1-methyl-2-oxopropyl, 2-oxopentyl, 3-oxopentyl, 1-methyl-2-oxobutyl, 1-methyl-3-oxobutyl, 2-oxohexyl, 3-oxohexyl, 4-oxohexyl, 2-oxoheptyl, 3-oxoheptyl, 4-oxoheptyl, 4-oxoheptyl and the like;

alkyl substituted by =S (thioxo group) e.g. 2-thioxopropyl, 2-thioxobutyl, 3-thioxobutyl, 1-methyl-2-thioxopropyl, 2-thioxopentyl, 3-thioxopentyl, 1-methyl-2-thioxobutyl, 1-methyl-3-thioxobutyl, 2-thioxohexyl, 3-thioxohexyl, 4-thioxohexyl, 2-thioxoheptyl, 3-thioxoheptyl, 4-thioxoheptyl, 4-thioxoheptyl and the like;

alkyl substituted by =$NR^a$, preferably a group of the type in which $R^a$ is hydrogen or $C_1$-$C_4$-alkyl, e.g. 2-iminopropyl, 2-iminobutyl, 3-iminobutyl, 1-methyl-2-iminopropyl, 2-iminopentyl, 3-iminopentyl, 1-methyl-2-iminobutyl, 1-methyl-3-imino-butyl, 2-imino-hexyl, 3-iminohexyl, 4-iminohexyl, 2-iminoheptyl, 3-iminoheptyl, 4-iminoheptyl, 4-imino-heptyl, 2-methyliminopropyl, 2-methyliminobutyl, 3-methyliminobutyl, 1-methyl-2-methyliminopropyl, 2-methyliminopentyl, 3-methyliminopentyl, 1-methyl-2-methyliminobutyl, 1-methyl-3-methyliminobutyl, 2-methyliminohexyl, 3-methyliminohexyl, 4-methyliminohexyl, 2-methyliminoheptyl, 3-methyliminoheptyl, 4-methyliminoheptyl, 4-methyliminoheptyl, 2-ethyliminopropyl, 2-ethyliminobutyl, 3-ethyliminobutyl, 1-methyl-2-ethyliminopropyl, 2-ethyliminopentyl, 3-ethyliminopentyl, 1-methyl-2-ethyliminobutyl, 1-methyl-3-ethyliminobutyl, 2-ethyliminohexyl, 3-ethyliminohexyl, 4-ethyliminohexyl, 2-ethyliminoheptyl, 3-ethyliminoheptyl, 4-ethyliminoheptyl, 4-ethyliminoheptyl, 2-propyl-iminopropyl, 2-propyliminobutyl, 3-propyliminobutyl, 1-methyl-2-propyliminopropyl, 2-propyliminopentyl, 3-propyliminopentyl, 1-methyl-2-propyliminobutyl, 1-methyl-3-propyliminobutyl, 2-propyliminohexyl, 3-propyliminohexyl, 4-propyliminohexyl, 2-propyliminoheptyl, 3-propyliminoheptyl, 4-propyliminoheptyl, 4-propyliminoheptyl and the like.

Alkoxy is an alkyl group bound via an oxygen atom. Examples of alkoxy are: methoxy, ethoxy, n-propoxy, 1-methylethoxy, butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethyl-propoxy, 1,2,2-trimethylpropoxy, 1-ethyl-1-methylpropoxy or 1-ethyl-2-methylpropoxy, hexoxy and also $R^A O{-}(CH_2CH_2CH_2CH_2O)_n{-}CH_2CH_2CH_2CH_2O{-}$
where $R^A$ is hydrogen or $C_1$-$C_4$-alkyl, preferably hydrogen, methyl or ethyl, and n is from 0 to 10, preferably from 0 to 3.

Alkylthio (alkylsulfanyl) is an alkyl group bound via a sulfur atom. Examples of alkylthio are methylthio, ethylthio, propylthio, butylthio, pentylthio and hexylthio.

Alkylsulfinyl is an alkyl group bound via an S(=O) group.

Alkylsulfonyl is an alkyl group bound via an S(=O)$_2$ group.

Aryl-substituted alkyl radicals ("arylalkyl") have at least one unsubstituted or substituted aryl group as defined below. Suitable substituents on the aryl group are those mentioned below. The alkyl group in "arylalkyl" can bear at least one further substituent as defined above and/or be interrupted by one or more nonadjacent heteroatoms or heteroatom-comprising groups selected from among —O—, —S—, —NR$^a$— and —SO$_2$—. Arylalkyl is preferably phenyl-$C_1$-$C_{10}$-alkyl, particularly preferably phenyl-$C_1$-$C_4$-alkyl, e.g. benzyl, 1-phenethyl, 2-phenethyl, 1-phenprop-1-yl, 2-phenprop-1-yl, 3-phenprop-1-yl, 1-phenbut-1-yl, 2-phenbut-1-yl, 3-phenbut-1-yl, 4-phenbut-1-yl, 1-phenbut-2-yl, 2-phenbut-2-yl, 3-phenbut-2-yl, 4-phenbut-2-yl, 1-(phenmeth)-eth-1-yl, 1-(phenmethyl)-1-(methyl)-eth-1-yl or -(phenmethyl)-1-(methyl)-prop-1-yl; preferably benzyl and 2-phenethyl.

For the purposes of the present invention, the expression "alkenyl" comprises straight-chain and branched alkenyl groups which can, depending on the length oft the chain, have one or more double bonds (e.g. 1, 2, 3, 4 or more than 4). Preference is given to $C_2$-$C_{18}$-alkenyl, particularly preferably $C_2$-$C_{12}$-alkenyl groups. The expression "alkenyl" also comprises substituted alkenyl groups which may bear one or more (e.g. 1, 2, 3, 4, 5 or more than 5) substituents. Suitable substituents are, for example, selected from among =O, =S, =NR$^a$, cycloalkyl, cycloalkyloxy, polycyclyl, polycyclyloxy, hetero-cycloalkyl, aryl, aryloxy, arylthio, hetaryl, halogen, hydroxy, SH, COOH, carboxylate, SO$_3$H, sulfonate, alkylsulfinyl, alkylsulfonyl, NE$^3$E$^4$, nitro and cyano, where E$^3$ and E$^4$ are each, independently of one another, hydrogen, alkyl, cycloalkyl, heterocycloalkyl, aryl or hetaryl The expression "alkenyl" also comprises alkenyl radicals whose carbon chain may be interrupted by one or more nonadjacent heteroatoms or heteroatom-comprising groups which are preferably selected from among —O—, —S—, —NR$^a$— and —SO$_2$—.

Alkenyl is then, for example, ethenyl (vinyl), 1-propenyl, 2-propenyl, 1-methylethenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, penta-1,3-dien-1-yl, hexa-1,4-dien-1-yl, hexa-1,4-dien-3-yl, hexa-1,4-dien-6-yl, hexa-1,5-dien-1-yl, hexa-1,5-dien-3-yl, hexa-1,5-dien-4-yl, hepta-1,4-dien-1-yl, hepta-1,4-dien-3-yl, hepta-1,4-dien-6-yl, hepta-1,4-dien-7-yl, hepta-1,5-dien-1-yl, hepta-1,5-dien-3-yl, hepta-1,5-dien-4-yl, hepta-1,5-dien-7-yl, hepta-1,6-dien-1-yl, hepta-1,6-dien-3-yl, hepta-1,6-dien-4-yl, hepta-1,6-dien-5-yl, hepta-1,6-dien-2-yl, octa-1,4-dien-1-yl, octa-1,4-dien-2-yl, octa-1,4-dien-3-yl, octa-1,4-dien-6-yl, octa-1,4-dien-7-yl, octa-1,5-dien-1-yl, octa-1,5-dien-3-yl, octa-1,5-dien-4-yl, octa-1,5-dien-7-yl, octa-1,6-dien-1-yl, octa-1,6-dien-3-yl, octa-1,6-dien-4-yl, octa-1,6-dien-5-yl, octa-1,6-dien-2-yl, deca-1,4-dienyl, deca-1,5-dienyl, deca-1,6-dienyl, deca-1,7-dienyl, deca-1,8-dienyl, deca-2,5-dienyl, deca-2,6-dienyl, deca-2,7-dienyl, deca-2,8-dienyl and the like.

For the purposes of the present invention, the expression "cycloalkyl" comprises both unsubstituted and substituted monocyclic saturated hydrocarbon groups which generally have from 3 to 12 ring carbons, ($C_3$-$C_{12}$-cycloalkyl groups) such as cyclopropyl, cyclobutyl, cyclopentyl, cyclohexyl, cycloheptyl, cyclooctyl, cyclononyl, cyclodecyl, cycloundecyl or cyclododecyl, in particular $C_5$-$C_{12}$-cycloalkyl. Suitable substituents are generally selected from among the substituents mentioned above for alkyl groups, alkoxy and alkylthio. Substituted cycloalkyl groups can have one or more (e.g. 1, 2, 3, 4, 5 or more than 5) substituents, and in the case of halogen the cycloalkyl radical is partially or completely substituted by halogen.

Examples of cycloalkyl groups are cyclopentyl, 2- and 3-methylcyclopentyl, 2- and 3-ethylcyclopentyl, chloropentyl, dichloropentyl, dimethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, chlorohexyl, dimethylcyclohexyl, diethylcyclohexyl, methoxy-cyclohexyl, dimethoxycyclohexyl, diethoxycyclohexyl, butoxycyclohexyl, methyl-thiocyclohexyl, chlorocyclohexyl, dichlorocyclohexyl, cycloheptyl, 2-, 3- and 4-methyl-cycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl, 3-, 4- and 5-propylcyclooctyl, partially fluorinated cycloalkyl and perfluorinated cycloalkyl of the formula $C_n F_{2(n-a)-}(1-b)H_{2a-b}$ where n=5 to 12, $0 \leq a \leq n$ and b=0 or 1.

Cycloalkyloxy is a cycloalkyl group as defined above bound via oxygen.

The expression "cycloalkenyl" comprises unsubstituted and substituted, singly or doubly unsaturated hydrocarbon groups having from 3 to 5, up to 8, up to 12, preferably from 5 to 12, ring carbons, e.g. cyclopent-1-en-1-yl, cyclopent-2-en-1-yl, cyclopent-3-en-1-yl, cyclohex-1-en-1-yl, cyclohex- 2-en-1-yl, cyclohex-3-en-1-yl, cyclohexa-2,5-dien-1-yl and the like. Suitable substituents are those mentioned above for cycloalkyl.

Cycloalkenyloxy is a cycloalkenyl group as defined above bound via oxygen.

For the purposes of the present invention, the expression "polycyclyl" comprises in the broadest sense compounds which comprise at least two rings, regardless of how these rings are linked. These can be carbocyclic and/or heterocyclic rings. The rings can be saturated or unsaturated. The rings can be linked via a single or double bond ("multiring compounds") joined by fusion ("fused ring systems") or bridged ("bridged ring systems", "cage compounds"). Preferred polycyclic compounds are bridged ring systems and fused ring systems. Fused ring systems can be aromatic, hydroaromatic and cyclic compounds joined by fusion (fused compounds). Fused ring systems comprise two, three or more than three rings. Depending on the way in which the rings are joined in fused ring systems, a distinction is made between ortho-fusion, i.e. each ring shares an edge or two atoms with each adjacent ring, and peri-fusion in which a carbon atom belongs to more than two rings. Among fused ring systems, preference is given to ortho-fused ring systems. For the purposes of the present invention, bridged ring systems include systems which do not belong to the multiring ring systems nor to the fused ring systems and in which at least two ring atoms belong to at least two different rings. Among the bridged ring systems, a distinction is made according to the number of ring opening reactions which are formally required to obtain an open-chain compound between bicyclo, tricyclo, tetracyclo compounds, etc., which comprise two, three, four, etc., rings. The expression "bicycloalkyl" comprises bicyclic hydrocarbon radicals which preferably have from 5 to 10 carbon atoms, e.g. bicyclo[2.2.1]hept-1-yl, bicyclo[2.2.1]hept-2-yl, bicyclo[2.2.1]hept-7-yl, bicyclo[2.2.2]oct-1-yl, bicyclo [2.2.2]oct-2-yl, bicyclo[3.3.0]octyl, bicyclo[4.4.0]decyl and the like. The expression "bicycloalkenyl" comprises monounsaturated, bicyclic hydrocarbon radicals which preferably have from 5 to 10 carbon atoms, e.g. bicyclo[2.2.1] hept-2-en-1-yl.

For the purposes of the present invention, the expression "aryl" comprises aromatic hydrocarbon radicals which have one or more rings and may be unsubstituted or substituted. The term aryl generally refers to hydrocarbon radicals having from 6 to 10, up to 14, up to 18, preferably from 6 to 10, ring carbons. Aryl is preferably unsubstituted or substituted phenyl, naphthyl, anthracenyl, phenanthrenyl, naphthacenyl, chrysenyl, pyrenyl, etc., and particularly preferably phenyl or naphthyl. Substituted aryls can, depending on the number and size of their ring systems, have one or more (e.g. 1, 2, 3, 4, 5 or more than 5) substituents. These are preferably selected independently from among alkyl, alkoxy, cycloalkyl, cycloalkyloxy, heterocycloalkyl, aryl, aryloxy, arylthio, hetaryl, halogen, hydroxy, SH, alkylthio, alkylsulfinyl, alkylsulfonyl, COOH, carboxylate, $SO_3H$, sulfonate, $NE^5E^6$, nitro and cyano, where $E^5$ and $E^6$ are each, independently of one another, hydrogen, alkyl, cycloalkyl, cycloalkyloxy, polycyclyl, polycyclyloxy, heterocycloalkyl, aryl, aryloxy or hetaryl. Aryl is particularly preferably phenyl which, if it is substituted, can generally bear 1, 2, 3, 4 or 5 substituents, preferably 1, 2 or 3 substituents.

Aryl which bears one or more radicals is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butyl-phenyl, 2,4-, 2,5-, 3,5- and 2,6-dibutylphenyl, 2,4,6-tributylphenyl, 2-, 3- and 4-isobutyl-phenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl, 2,4,6-tri-tert-butylphenyl and 2-, 3-, 4-dodecylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxy-phenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl, 2-, 3- and 4-butoxyphenyl, 2-, 3-, 4-hexyloxy-phenyl; 2-, 3-, 4-chlorophenyl, 2,4-, 2,5-, 3,5- and 2,6-dichlorophenyl, trichlorophenyl, 2-, 3-, 4-fluorophenyl, 2,4-, 2,5-, 3,5- and 2,6-difluorophenyl, trifluorophenyl, for example 2, 4,6-trifluorophenyl, tetrafluorophenyl, pentafluorophenyl, 2-, 3- and 4-cyano-phenyl; 2-nitrophenyl, 4-nitrophenyl, 2,4-dinitrophenyl, 2,6-dinitrophenyl; 4-dimethyl-aminophenyl; 4-acetylphenyl; methoxyethylphenyl, ethoxymethylphenyl; methyl-thiophenyl, isopropylthiophenyl or tert-butylthiophenyl; methylnaphthyl; isopropyl-naphthyl or ethoxynaphthyl. Examples of substituted aryl in which two substituents bound to adjacent carbon atoms of the aryl ring form a fused ring or fused ring system are indenyl and fluorenyl.

For the purposes of the present invention, the expression "aryloxy" refers to aryl bound via an oxygen atom.

For the purposes of the present invention, the expression "arylthio" refers to aryl bound via a sulfur atom.

For the purposes of the present invention, the expression "heterocycloalkyl" comprises nonaromatic, unsaturated or fully saturated, cycloaliphatic groups which generally have from 5 to 8 ring atoms, for example 5 or 6 ring atoms, and in which 1, 2 or 3 of the ring carbons have been replaced by heteroatoms selected from among oxygen, nitrogen, sulfur and an —$NR^a$— group and which are unsubstituted or substituted by one or more, for example, 1, 2, 3, 4, 5 or 6, $C_1$-$C_6$-alkyl groups. Examples of such heterocyclo-aliphatic groups are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothienyl, dihydrothienyl, tetrahydrofuranyl, dihydrofuranyl, tetrahydropyranyl, 1,2-oxazolin-5-yl, 1,3-oxazolin-2-yl and dioxanyl. Nitrogen-comprising heterocycloalkyl can in principle be bound either via a carbon atom or via a nitrogen atom.

For the purposes of the present invention, the expression "heteroaryl (hetaryl)" comprises unsubstituted or substituted, heteroaromatic groups which have one or more rings and generally have from 5 to 14 ring atoms, preferably 5 or 6 ring atoms, in which 1, 2 or 3 of the ring carbons have been replaced by one, two, three or four heteroatoms selected from among O, N, —$NR^a$— and S, e.g. furyl, thienyl, oxazolyl, isoxazolyl, thiazolyl, isothiazolyl, benzofuranyl, benzthiazolyl, benzimidazolyl, pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl, where these heterocycloaromatic groups may, if they are substituted, generally bear 1, 2 or 3 substituents. The substituents are generally selected from among $C_1$-$C_6$-alkyl, $C_1$-$C_6$-alkoxy, hydroxy, carboxy, halogen and cyano.

5- to 7-membered nitrogen-comprising heterocycloalkyl or heteroaryl radicals which may optionally comprise further heteroatoms are, for example, pyrrolyl, pyrazolyl, imidazolyl, triazolyl, pyrrolidinyl, pyrazolinyl, pyrazolidinyl, imidazolinyl, imidazolidinyl, pyridinyl, pyridazinyl, pyrimidinyl, pyrazinyl, triazinyl, piperidinyl, piperazinyl, oxazolyl, isoxazolyl, thiazolyl, isothiazolyl, indolyl, quinolinyl, isoquinolinyl or quinaldinyl which may be unsubstituted or substituted as mentioned above.

Halogen is fluorine, chlorine, bromine or iodine.

For the purposes of the present invention, carboxylate and sulfonate are preferably a derivative of a carboxylic acid function or a sulfonic acid function, in particular a metal carboxylate or sulfonate, a carboxylic ester or sulfonic ester function or a carboxamide or sulfonamide function. These include, for example, esters with $C_1$-$C_4$-alkanols such as methanol, ethanol, n-propanol, isopropanol, n-butanol, sec-butanol and tert-butanol.

For the purposes of the present invention, the expression "acyl" refers to alkanoyl, hetaroyl or aroyl groups which generally have from 1 to 11, preferably from 2 to 8, carbon atoms, for example the formyl, acetyl, propanoyl, butanoyl, pentanoyl, hexanoyl, heptanoyl, 2-ethylhexanoyl, 2-propyl-heptanoyl, benzoyl or naphthoyl group.

The radicals $E^1$ and $E^2$, $E^3$ and $E^4$, $E^5$ and $E^6$ are selected independently from among hydrogen, alkyl, cycloalkyl and aryl. The groups $NE^1E^2$, $NE^3E^4$ and $NE^5E^6$ are preferably N,N-dimethylamino, N,N-diethylamino, N,N-dipropylamino, N,N-diisopropyl-amino, N,N-di-n-butylamino, N,N-di-tert-butylamino, N,N-dicyclohexylamino or N,N-diphenylamino.

All ionic liquids based on multiatomic anions are in principle suitable for use in the process of the invention.

Preferred ionic liquids are
(A) Salts of the General Formula (I)

$$[A]_n^+[Y]^{n-} \qquad \text{(I)},$$

where n is 1, 2, 3 or 4, $[A]^+$ is a quaternary ammonium cation, an oxonium cation, a sulfonium cation or a phosphonium cation and $[Y]^{n-}$ is a multiatomic, monovalent, divalent, trivalent or tetravalent anion or a mixture of these anions;
(B) Mixed Salts Of The General Formulae (II)

   (II.a), where n=2,

   (II.b), where n=3,

   (II.c), where n=4, where $[A^1]^+$, $[A^2]^+$, $[A^3]^+$ and $[A^4]^+$ are selected independently from among the groups mentioned for $[A]^+$ and $[Y]^{n-}$ is as defined under (A); or
(C) Mixed Salts of the General Formulae (III)

   (III.a), where n=4,

   (III.b), where n=4,

   (III.c), where n=4,

   (III.d), where n=3,

   (III.e), where m=3,

   (III.f), where n=2,

   (III.g), where n=4,

   (III.h), where n=4

   (III.i), where n=4,

   (III.j), where n=3, where $[A^1]^+$, $[A^2]^+$ and $[A^3]^+$ are selected independently from among the groups mentioned for $[A]^+$, $[Y]^{n-}$ is as defined under (A) and $[M^1]^+$, $[M^2]^+$, $[M^3]^+$ are monovalent metal cations, $[M^4]^{2+}$ are divalent metal cations and $[M^5]^{3+}$ are trivalent metal cations.

Preference is given to salts of groups A and B, particularly preferably group A.

The metal cations $[M^1]^+$, $[M^2]^+$, $[M^3]^+$, $[M^4]^{2+}$ and $[M^5]^{3+}$ mentioned in the formulae (III.a) to (III.j) are generally metal cations of groups 1, 2, 6, 7, 8, 9, 10, 11, 12, 13 and 14 of the Periodic Table. Suitable metal cations are, for example, $Li^+$, $Na^+$, $K^+$, $Cs^+$, $Mg^{2+}$, $Ca^{2+}$, $Ba^{2+}$, $Cr^{3+}$, $Fe^{2+}$, $Fe^{3+}$, $Co^{2+}$, $Ni^{2+}$, $Cu^{2+}$, $Ag^+$, $Zn^{2+}$ and $Al^{3+}$.

Compounds suitable for the formation of the cations $[A]^+$ of ionic liquids are described, for example, in DE 102 02 838 A1. These compounds preferably comprise at least one heteroatom, e.g. from 1 to 10 heteroatoms, which is/are preferably selected from among nitrogen, oxygen, phosphorus and sulfur atoms. Preference is given to compounds which comprise at least one nitrogen atom and optionally in addition at least one further heteroatom different from nitrogen. Preference is given to compounds which comprise at least one nitrogen atom, particularly preferably from 1 to 10 nitrogen atoms, in particular from 1 to 5 nitrogen atoms, very particularly preferably from 1 to 3 nitrogen atoms and especially 1 or 2 nitrogen atoms. The latter nitrogen compounds can comprise further heteroatoms such as oxygen, sulfur or phosphorus atoms.

The nitrogen atom is, for example, a suitable carrier of the positive charge in the cation of the ionic liquid. If the nitrogen atom is the carrier of the positive charge in the cation of the ionic liquid, a cation can firstly be produced by quaternization of the nitrogen atom of, for instance, an amine or nitrogen heterocycle in the synthesis of the ionic liquids. Quaternization can be effected by protonation of the nitrogen atom. Depending on the protonation reagent used, salts having different anions are obtained. In cases in which it is not possible to form the desired anion in the quaternization itself, this can be brought about in a further step of the synthesis. Starting from, for example, an ammonium halide, the halide can be reacted with a Lewis acid, forming a complex anion from the halide and Lewis acid. As an alternative, replacement of a halide ion by the desired anion is possible. This can be achieved by addition of a metal salt with precipitation of the metal halide formed, by means of an ion exchanger or by displacement of the halide ion by a strong acid (with liberation of the hydrogen halide). Suitable methods are described, for example, in Angew. Chem. 2000, 112, pp. 3926-3945, and the references cited therein.

Preference is given to compounds which comprise at least one five- or six-membered heterocycle, in particular a five-membered heterocycle, which has at least one nitrogen atom and also, if appropriate, an oxygen or sulfur atom. Particular preference is given to compounds which comprise at least one five- or six-membered heterocycle which has one, two or three nitrogen atoms and a sulfur or oxygen atom, very particularly preferably compounds having two nitrogen atoms. Further preference is given to aromatic heterocycles.

Particularly preferred compounds have a molar mass of less than 1000 g/mol, very particularly preferably less than 600 g/mol and in particular less than 400 g/mol.

Preferred cations are selected from among the compounds of the formulae (IV.a) to (IV.w),

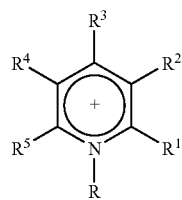
(IV.a)

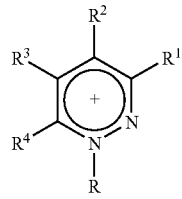
(IV.b)

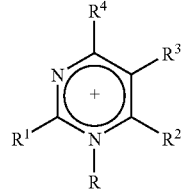
(IV.c)

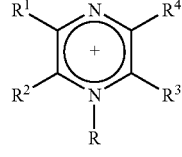
(IV.d)

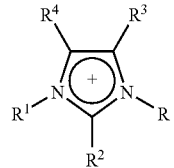
(IV.e)

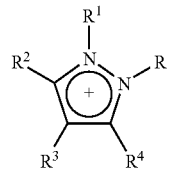
(IV.f)

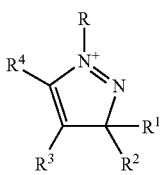
(IV.g)

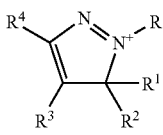
(IV.g')

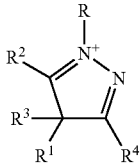
(IV.h)

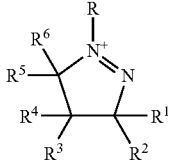
(IV.i)

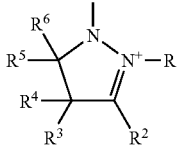
(IV.j)

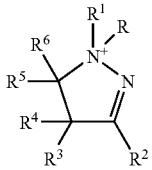
(IV.j')

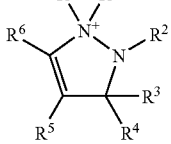
(IV.k)

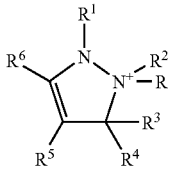
(IV.k')

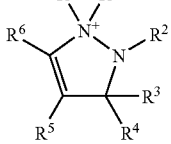
(IV.l)

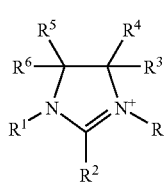
(IV.m)
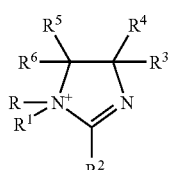
(IV.m′)
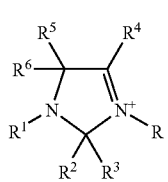
(IV.n)
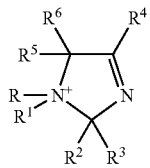
(IV.n′)
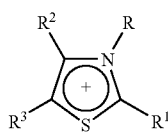
(IV.o)
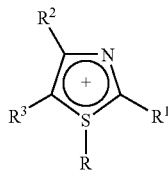
(IV.o′)
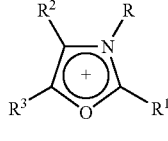
(IV.p)
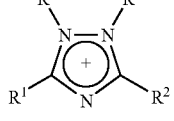
(IV.q)
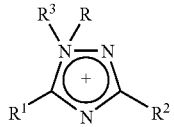
(IV.q′)
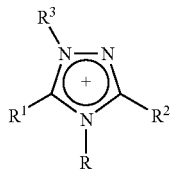
(IV.q″)
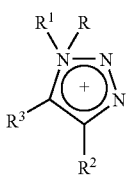
(IV.r)
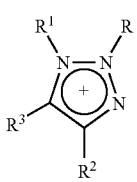
(IV.r′)
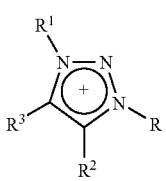
(IV.r″)
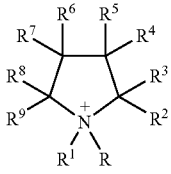
(IV.s)
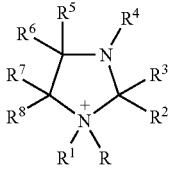
(IV.t)
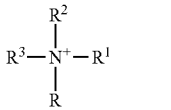
(IV.u)
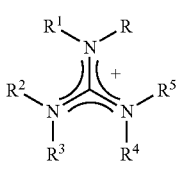
(IV.v)
(IV.w)
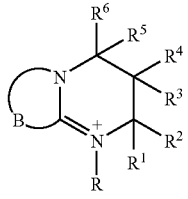
(IV.x.1)

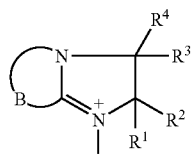

(IV.x.2)

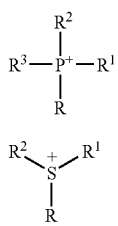

(IV.y)

(IV.z)

and oligomers comprising these structures, where

R is hydrogen, alkyl, alkenyl, cycloalkyl, cycloalkenyl, polycyclyl, heterocycloalkyl, aryl or heteroaryl;

radicals $R^1$, $R^2$, $R^3$, $R^4$, $R^5$, $R^6$, $R^7$, $R^8$ and $R^9$ which are bound to a ring carbon are each, independently of one another, hydrogen, a sulfo group, COOH, carboxylate, sulfonate, acyl, alkoxycarbonyl, cyano, halogen, hydroxyl, SH, nitro, $NE^1E^2$, alkyl, alkoxy, alkylthio, alkylsulfinyl, alkylsulfonyl, alkenyl, cycloalkyl, cycloalkyloxy, cycloalkenyl, cycloalkenyloxy, polycyclyl, polycyclyloxy, heterocycloalkyl, aryl, aryloxy or heteroaryl, where $E^1$ and $E^2$ are each, independently of one another, hydrogen, alkyl, cycloalkyl, heterocycloalkyl, aryl or hetaryl, radicals $R^1$, $R^2$, $R^3$, $R^4$, $R^5$, $R^6$, $R^7$, $R^8$ and $R^9$ which are bound to a ring heteroatom are each hydrogen, $SO_3H$, $NE^1E^2$, alkyl, alkoxy, alkenyl, cycloalkyl, cycloalkenyl, polycyclyl, heterocycloalkyl, aryl or heteroaryl, where $E^1$ and $E^2$ are each, independently of one another, hydrogen, alkyl, cycloalkyl, heterocycloalkyl, aryl or hetaryl, or two adjacent radicals $R^1$ to $R^9$ together with the ring atoms to which they are bound may also form at least one fused-on, saturated, unsaturated or aromatic ring or a ring system having from 1 to 30 carbon atoms, where the ring or the ring system may have from 1 to 5 nonadjacent heteroatoms or heteroatom-comprising groups and the ring or the ring system may be unsubstituted or substituted, two geminal radicals $R^1$ to $R^9$ may also together be =O, =S or $=NR^b$, where $R^b$ is hydrogen, alkyl, cycloalkyl, aryl or heteroaryl, and $R^1$ and $R^3$ or $R^3$ and $R^5$ in the compounds of the formula (IV.x.1) may together also represent the second part of a double bond between the ring atoms bearing these radicals, B in the compounds of the formulae (IV.x.1) and (IV.x.2) together with the C—N group to which it is bound forms a 4- to 8-membered, saturated or unsaturated or aromatic ring which may optionally be substituted and/or may optionally have further heteroatoms or heteroatom-comprising groups and/or may comprise further fused-on, saturated, unsaturated or aromatic carbocycles or heterocycles.

As regards the general meaning of the abovementioned radicals carboxylate, sulfonate, acyl, alkoxycarbonyl, halogen, $NE^1E^2$, alkyl, alkoxy, alkylthio, alkylsulfinyl, alkylsulfonyl, alkenyl, cycloalkyl, cycloalkyloxy, cycloalkenyl, cycloalkenyloxy, polycyclyl, polycyclyloxy, heterocycloalkyl, aryl, aryloxy or heteroaryl, what has been said above applies in full. Radicals $R^1$ to $R^9$ in the abovementioned formulae (IV) which are bound to a carbon atom and have a heteroatom or a heteroatom-comprising group can also be bound directly via a heteroatom to the carbon atom.

If two adjacent radicals $R^1$ to $R^9$ together with the ring atoms to which they are bound form at least one fused-on, saturated, unsaturated or aromatic ring or a ring system having from 1 to 30 carbon atoms, where the ring or ring system can have from 1 to 5 nonadjacent heteroatoms or heteroatom-comprising groups and the ring or the ring system may be unsubstituted or substituted, these radicals can together as fused-on building blocks preferably be 1,3-propylene, 1,4-butylene, 1,5-pentylene, 2-oxa-1,3-propylene, 1-oxa-1,3-propylene, 2-oxa-1,3-propylene, 1-oxa-1,3-propenylene, 3-oxa-1,5-pentylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

The radical R is preferably unsubstituted $C_1$-$C_{18}$-alkyl such as methyl, ethyl, 1-propyl, 2-propyl, 1-butyl, 2-butyl, 2-methyl-1-propyl (isobutyl), 2-methyl-2-propyl (tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl, 1-octyl, 1-nonyl, 1-decyl, 1-undecyl, 1-dodecyl, 1-tetradecyl, 1-hexadecyl and 1-octadecyl;

$C_1$-$C_{18}$-alkyl substituted by one or more hydroxy, halogen, phenyl, cyano, $C_1$-$C_6$-alkoxycarbonyl and/or $SO_3H$ groups, especially hydroxy-$C_1$-$C_{18}$-alkyl such as 2-hydroxyethyl or 6-hydroxyhexyl; phenyl-$C_1$-$C_{18}$-alkyl, such as benzyl, 3-phenyl-propyl; cyano-$C_1$-$C_{18}$-alkyl, such as 2-cyanoethyl; $C_1$-$C_6$-alkoxy-$C_1$-$C_{18}$-alkyl, such as 2-(methoxycarbonyl)ethyl, 2-(ethoxycarbonyl)ethyl or 2-(n-butoxycarbonyl)-ethyl; $C_1$-$C_{18}$-fluoroalkyl such as trifluoromethyl, difluoromethyl, fluoromethyl, pentafluoroethyl, heptafluoropropyl, heptafluoroisopropyl, nonafluorobutyl, nonafluoroisobutyl, undecylfluoropentyl, undecylfluoroisopentyl; sulfo-$C_1$-$C_{18}$-alkyl such as 3-sulfopropyl;

hydroxyethyloxyalkyl, radicals of oligoalkylene and polyalkylene glycols such as polyethylene glycols and polypropylene glycols and their oligomers having 2 to 100 units and a hydrogen or a $C_1$-$C_8$-alkyl as end group, for example $R^AO$—$(CHR^B$—$CH_2$—$O)_n$—$CHR^B$—$CH_2$— where $R^A$ and $R^B$ are preferably each hydrogen, methyl or ethyl and n is preferably from 0 to 3, in particular 3-oxabutyl, 3-oxapentyl, 3,6-dioxaheptyl, 3,6-dioxaoctyl, 3,6,9-trioxadecyl, 3,6,9-trioxa-undecyl, 3,6,9,12-tetraoxamidecyl and 3,6,9,12-tetraoxatetradecyl; and $C_2$-$C_6$-alkenyl such as vinyl or propenyl.

The radical R is particularly preferably linear $C_1$-$C_{18}$-alkyl, for example methyl, ethyl, 1-propyl, 1-butyl, 1-pentyl, 1-hexyl, 1-heptyl, 1-octyl, 1-decyl, 1-dodecyl, 1-tetradecyl, 1-hexadecyl, 1-octadecyl, very particularly preferably methyl, ethyl, 1-butyl and 1-octyl, or $CH_3O$—$(CH_2CH_2O)_n$—$CH_2CH_2$— and $CH_3CH_2O$—$(CH_2CH_2O)_m$—$CH_2CH_2$— where m is 0 or 3.

Preference is given to the radicals $R^1$ to $R^9$ each being, independently of one another, hydrogen;

halogen;

a functional group selected from among hydroxy, alkoxy, alkylthio, carboxyl, -COOH, sulfonate, cyano, acyl, alkoxycarbonyl, $NE^1E^2$ and nitro, where $E^1$ and $E^2$ are as defined above;

$C_1$-$C_{18}$-alkyl which is unsubstituted or substituted as defined above and/or may, as defined above, be interrupted by at least one heteroatom or heteroatom-comprising group;

$C_2$-$C_{18}$-alkenyl which is unsubstituted or substituted as defined above and/or may, as defined above, be interrupted by at least one heteroatom;

$C_6$-$C_{10}$-aryl which is unsubstituted or substituted as defined above;

$C_5$-$C_{12}$-cycloalkyl which is unsubstituted or substituted as defined above;

polycyclyl which is unsubstituted or substituted as defined above;

$C_5$-$C_{12}$-cycloalkenyl which is unsubstituted or substituted as defined above;

heterocycloalkyl having 5 or 6 ring atoms, where the ring comprises, apart from ring carbons, 1, 2 or 3 heteroatoms or heteroatom-comprising groups selected from among oxygen, nitrogen, sulfur and $NR^a$ and is unsubstituted or substituted as defined above;

heteroaryl having from 5 to 10 ring atoms, where the ring has, apart from ring carbons, 1, 2 or 3 heteroatoms or heteroatom-comprising groups selected from among oxygen, nitrogen, sulfur and $NR^a$ and is unsubstituted or substituted as defined above.

Preference is likewise given to two adjacent radicals $R^1$ to $R^9$ together with the ring atoms to which they are bound forming at least one fused-on, saturated, unsaturated or aromatic ring or ring system having from 1 to 12 carbon atoms, where the ring or ring system may have from 1 to 5 nonadjacent heteroatoms or heteroatom-comprising groups which are preferably selected from among oxygen, nitrogen, sulfur and $NR^a$ and the ring or the ring system may be unsubstituted or substituted, where the substituents are preferably selected independently from among alkoxy, cycloalkyl, cycloalkoxy, polycyclyl, polycyclyloxy, heterocycloalkyl, aryl, aryloxy, arylthio, heteroaryl halogen, hydroxy, SH, =O, =S, =$NR^a$, COOH, carboxylate, —$SO_3H$, sulfonate, $NE^1E^2$, nitro and cyano, where $E^1$ and $E^2$ are each, independently of one another, hydrogen, alkyl, cycloalkyl, heterocycloalkyl, aryl or hetaryl.

If $R^1$ to $R^9$ are alkoxy, then $R^1$ to $R^9$ are preferably methoxy or ethoxy or $R^AO$—$(CH_2CH_2CH_2CH_2O)_n$—$CH_2CH_2CH_2CH_2O$— where $R^A$ and $R^B$ are preferably each hydrogen, methyl or ethyl and n is preferably from 0 to 3.

If $R^1$ to $R^9$ are acyl, then $R^1$ to $R^9$ are preferably formyl or $C_1$-$C_4$-alkylcarbonyl, in particular formyl or acetyl.

If $R^1$ to $R^9$ are $C_1$-$C_{15}$-alkyl, then $R^1$ to $R^9$ are preferably unsubstituted $C_1$-$C_{18}$-alkyl such as methyl, ethyl, 1-propyl, 2-propyl, 1-butyl, 2-butyl, 2-methyl-1-propyl (isobutyl), 2-methyl-2-propyl (tert-butyl), 1-pentyl, 2-pentyl, 3-pentyl, 2-methyl-9-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, 2-ethylhexyl, 2,4,4-trimethyl-pentyl, 1,1,3,3-tetramethylbutyl, 1-nonyl, 1-decyl, 1-undecyl, 1-dodecyl, 1-tridecyl, 1-tetradecyl, 1-pentadecyl, 1-hexadecyl, 1-heptadecyl, 1-octadecyl;

$C_1$-$C_{18}$-haloalkyl, especially $C_1$-$C_{18}$-fluoroalkyl, for example trifluoromethyl, difluoromethyl, fluoromethyl, pentafluoroethyl, heptafluoropropyl, heptafluoroisopropyl, nonafluorobutyl, nonafluoroisobutyl, undecylfluoropentyl, undecylisopentyl, $C_6F_{13}$, $C_8F_{17}$, $C_{10}F_{21}$, $C_{12}F_{25}$, especially $C_1$-$C_{18}$-chloroalkyl such as chloromethyl, 2-chloroethyl, trichloromethyl, 1,1-dimethyl-2-chloroethyl;

amino-$C_1$-$C_{18}$-alkyl such as 2-aminoethyl, 2-aminopropyl, 3-aminopropyl, 4-aminobutyl, 6-aminohexyl, $C_1$-$C_6$-alkylamino-$C_1$-$C_{18}$-alkyl such as 2-methylaminoethyl, 2-methylaminopropyl, 3-methylaminopropyl, 4-methylaminobutyl, 6-methylaminohexyl;

di($C_1$-$C_8$-alkyl)-$C_1$-$C_{18}$-alkyl such as 2-dimethylaminoethyl, 2-dimethylaminopropyl, 3-dimethylaminopropyl, 4-dimethylaminobutyl, 6-dimethylaminohexyl, cyano-$C_1$-$C_{18}$-alkyl such as 2-cyanoethyl, 2-cyanopropyl, $C_1$-$C_{10}$-alkoxy-$C_1$-$C_{18}$-alkyl such as methoxymethyl, 2-methoxyethyl, 2-methoxypropyl, 3-methoxypropyl, 2-methoxyisopropyl, 4-methoxybutyl, 6-methoxyhexyl, 2-ethoxyethyl, 2-ethoxypropyl, 3-ethoxypropyl, 4-ethoxybutyl, 6-ethoxyhexyl, 2-isopropoxyethyl, 2-butoxyethyl, 2-butoxypropyl, 2-octyloxyethyl, 5-methoxy-3-oxa-pentyl, 8-methoxy-3,6-dioxaoctyl, 7-methoxy-4-oxaheptyl, 11-methoxy-4,8-dioxaundecyl, 9-methoxy-5-oxanonyl, 9-methoxy-5-oxanonyl, 14-methoxy-5,10-dioxatetradecyl, 5-ethoxy-3-oxa-pentyl, 8-ethoxy-3,6-dioxaoctyl, 7-ethoxy-4-oxaheptyl, 11-ethoxy-4,8-dioxaundecyl, 9-ethoxy-5-oxanonyl or 14-ethoxy-5,10-oxatetradecyl, 15-methoxy-4,8,12-trioxa-pentadecyl, 11-methoxy-3,6,9-trioxaundecyl, 11-ethoxy-3,6,9-trioxaundecyl, 15-ethoxy-4,8,12-trioxapentadecyl;

di($C_1$-$C_{10}$-alkoxy-$C_1$-$C_{18}$-alkyl) such as diethoxymethyl or diethoxyethyl, $C_1$-$C_6$-alkoxycarbonyl-$C_1$-$C_{18}$-alkyl such as 2-(methoxycarbonyl)ethyl, 2-(ethoxycarbonyl)ethyl, 2-(n-butoxycarbonyl)ethyl, di($C_1$-$C_6$-alkoxycarbonyl)-$C_1$-$C_{18}$-alkyl such as 1,2-di(methoxycarbonyl)ethyl, hydroxy-$C_1$-$C_{18}$-alkyl such as 2-hydroxyethyl, 2-hydroxypropyl, 3-hydroxypropyl, 4-hydroxybutyl, 6-hydroxyhexyl, 2-hydroxy-2,2-dimethylethyl, 5-hydroxy-3-oxapentyl, 8-hydroxy-3,6-dioxaoctyl, 11-hydroxy-3,6,9-trioxaundecyl, 7-hydroxy-4-oxaheptyl, 11-hydroxy-4,8-dioxaundecyl, 15-hydroxy-4,8,12-trioxapentadecyl, 9-hydroxy-5-oxanonyl, 14-hydroxy-5,10-dioxatetradecyl;

$C_1$-$C_{12}$-alkylsulfanyl-$C_1$-$C_{18}$-alkyl such as butylthiomethyl, 2-dodecylthioethyl, $C_5$-$C_{12}$-cycloalkyl-$C_1$-$C_{18}$-alkyl such as cyclopentylmethyl, 2-cyclopentylethyl, 3-cyclopentylpropyl, cyclohexylmethyl, 2-cyclohexylethyl, 3-cyclohexylpropyl, phenyl-$C_1$-$C_{18}$-alkyl, where the phenyl part of phenyl-$C_1$-$C_{18}$-alkyl is unsubstituted or substituted by one, two, three or four substituents selected independently from among $C_1$-$C_6$-alkyl, halogen, $C_1$-$C_6$-alkoxy and nitro, e.g. benzyl (phenylmethyl), 1-phenylethyl, 2-phenylethyl, 3-phenylpropyl, p-tolylmethyl, 1-(p-butylphenyl)ethyl, p-chlorobenzyl, 2,4-dichlorobenzyl, p-methoxybenzyl, m-ethoxybenzyl, phenyl-$C(CH_3)_2$—, 2,6-dimethylphenylmethyl, diphenyl-$C_1$-$C_{18}$-alkyl such as diphenylmethyl (benzhydryl);

triphenyl-$C_1$-$C_{18}$-alkyl such as triphenylmethyl;

phenoxy-$C_1$-$C_{18}$-alkyl such as 2-phenoxyethyl, 2-phenoxypropyl, 3-phenoxypropyl, 4-phenoxybutyl, 6-phenoxyhexyl;

phenylthio-$C_1$-$C_{18}$-alkyl such as 2-phenylthioethyl.

If $R^1$ to $R^9$ are $C_2$-$C_{18}$-alkenyl, then $R^1$ to $R^9$ are preferably each $C_2$-$C_6$-alkenyl such as vinyl, 2-propenyl, 3-butenyl, cis-2-butenyl, trans-2-butenyl or $C_2$-$C_{18}$-alkenyl which may be partially or completely substituted by fluorine.

If $R^1$ to $R^9$ are $C_6$-$C_{10}$-aryl, then $R^1$ to $R^9$ are each preferably phenyl or naphthyl, where phenyl or naphthyl is unsubstituted or substituted by one, two, three or four substituents selected independently from among halogen, $C_1$-$C_{15}$-alkyl, $C_1$-$C_6$-alkoxy, $C_1$-$C_6$-alkylsulfanyl, $C_1$-$C_6$-alkoxy-$C_1$-$C_6$-alkyl, $C_1$-$C_6$-alkylcarbonyl, amino, $C_1$-$C_6$-alkylamino, di($C_1$-$C_8$-dialkyl)amino and nitro, e.g. phenyl, methylphenyl (tolyl), dimethylphenyl (xylyl) such as 2,6-dimethylphenyl, trimethylphenyl such as 2,4,6-trimethylphenyl, ethylphenyl, diethylphenyl, isopropylphenyl, tert-butylphenyl, dodecylphenyl, chlorophenyl, dichlorophenyl, trichlorophenyl, fluorophenyl, difluorophenyl, trifluorophenyl, tetrafluorophenyl, pentafluorophenyl, 2,6-dichlorophenyl, 4-bromophenyl, methoxyphenyl, dimethoxyphenyl, ethoxyphenyl, hexyloxyphenyl, 2,6-dimethoxyphenyl, 2-nitrophenyl, 4-nitrophenyl, 2,4-dinitrophenyl, 2,6-dinitrophenyl, 4-dimethylaminophenyl, 4-acetylphenyl, methoxyethylphenyl, ethoxymethylphenyl, methylthiophenyl, isopropylthiophenyl, tert-butylthiophenyl, α-naphthyl, β-naphthyl, methylnaphthyl, isopropylnaphthyl, chloronaphthyl, ethoxynaphthyl or partially fluorinated phenyl or perfluorinated phenyl.

If $R^1$ to $R^9$ are $C_5$-$C_{12}$-cycloalkyl, then $R^1$ to $R^9$ are preferably each unsubstituted cycloalkyl such as cyclopentyl or cyclohexyl;

$C_5$-$C_{12}$-cycloalkyl which is substituted by one or two substituents selected independently from among $C_1$-$C_6$-alkyl, $C_1$-$C_6$-alkoxy, $C_1$-$C_6$-alkylsulfanyl and chlorine, e.g. butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl; $C_5$-$C_{12}$-cycloalkyl which is completely or fully fluorinated.

If $R^1$ to $R^9$ are polycyclyl, then $R^1$ to $R^9$ are each preferably $C_5$-$C_{12}$-bicycloalkyl such as norbornyl or $C_5$-$C_{12}$-bicycloalkenyl such as norbornenyl.

If $R^1$ to $R^9$ are $C_5$-$C_{12}$-cycloalkenyl, then $R^1$ to $R^9$ are each preferably unsubstituted cycloalkenyl such as cyclopent-2-en-1-yl, cyclopent-3-en-1-yl, cyclohex-2-en-1-yl, cyclohex-1-en-1-yl, cyclohexa-2,5-dien-1-yl or partially or completely fluorinated cycloalkenyl.

If $R^1$ to $R^9$ are heterocycloalkyl having 5 or 6 ring atoms, then $R^1$ to $R^9$ are each preferably 1,3-dioxolan-2-yl, 1,3-dioxan-2-yl, 2-methyl-1,3-dioxolan-2-yl, 4-methyl-1,3-dioxolan-2-yl.

If $R^1$ to $R^9$ are heteroaryl, then $R^1$ to $R^9$ are each preferably furyl, thienyl, pyrryl, pyridyl, indolyl, benzoxazolyl, benzimidazolyl, benzothiazolyl. If hetaryl is substituted, it bears 1, 2 or 3 substituents selected independently from among $C_1$-$C_6$-alkyl, $C_1$-$C_6$-alkoxy and halogen, for example dimethylpyridyl, methylquinolyl, dimethylpyrryl, methoxyfuryl, dimethoxypyridyl or difluoropyridyl.

Particular preference is given to the radicals $R^1$ to $R^9$ each being, independently of one another, hydrogen;

unbranched or branched $C_1$-$C_{18}$-alkyl which may be unsubstituted or substituted by one or more hydroxy, halogen, phenyl, cyano, $C_1$-$C_6$-alkoxycarbonyl and/or sulfo groups, for example methyl, ethyl, 1-propyl, 2-propyl, 1-butyl, 2-butyl, 2-methyl-1-propyl (isobutyl), 2-methyl-2-propyl (tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl, 1-octyl, 1-nonyl, 1-decyl, 1-undecyl, 1-dodecyl, 1-tetradecyl, 1-hexadecyl, 1-octadecyl, 2-hydroxyethyl, benzyl, 3-phenylpropyl, 2-cyanoethyl, methoxycarbonylmethyl, ethoxycarbonylmethyl, n-butoxycarbonylmethyl, tert-butoxycarbonylmethyl, 2-(methoxycarbonyl)ethyl, 2-(ethoxycarbonyl)ethyl, 2-(n-butoxycarbonyl)ethyl, trifluoromethyl, difluoromethyl, fluoromethyl, pentafluoroethyl, heptafluoropropyl, heptafluoroisopropyl, nonafluorobutyl, nonafluoroisobutyl, undecylfluoropentyl, undecylfluoroisopentyl, 6-hydroxyhexyl and 3-sulfopropyl;

hydroxyethyloxyalkyl, radicals of oligoalkylene and polyalkylene glycols such as polyethylene glycols and polypropylene glycols and their oligomers having from 2 to 100 units and a hydrogen or a $C_1$-$C_8$-alkyl as end group, for example $R^AO$—$(CHR^B$—$CH_2O)_n$—$CHR^B$—$CH_2$- or $R^AO$—$(CH_2CH_2CH_2CH_2O)_n$—$CH_2CH_2CH_2CH_2O$— where $R^A$ and $R^B$ are each preferably hydrogen, methyl or ethyl and n is preferably from 0 to 3, in particular 3-oxabutyl, 3-oxapentyl, 3,6-dioxaheptyl, 3,6-dioxaoctyl, 3,6,9-trioxadecyl, 3,6,9-trioxaundecyl, 3,6,9,12-tetraoxamidecyl and 3,6,9,12-tetraoxatetradecyl;

$C_2$-$C_4$-alkenyl such as vinyl and allyl; and

N,N-di-$C_1$-$C_6$-alkylamino such as N,N-dimethylamino and N,N-diethylamino.

Very particular preference is given to the radicals $R^1$ to $R^9$ each being, independently of one another, hydrogen; $C_1$-$C_{15}$-alkyl such as methyl, ethyl, 1-butyl, 1-pentyl, 1-hexyl, 1-heptyl, 1-octyl; phenyl; 2-hydroxyethyl; 2-cyanoethyl; 2-(alkoxycarbonyl)ethyl such as 2-(methoxycarbonyl)ethyl, 2-(ethoxycarbonyl)ethyl or 2-(n-butoxycarbonyl)ethyl; N,N-($C_1$-$C_4$-dialkyl)amino such as N,N-dimethylamino or N,N-diethylamino; chlorine or a radical of oligoalkylene glycol, e.g. $CH_3O$—$(CH_2CH_2O)_n$—$CH_2CH_2$- or $CH_3CH_2O$—$(CH_2CH_2O)_n$—$CH_2CH_2$- where n is from 0 to 3.

Very particularly preferred pyridinium ions (IVa) are those in which one of the radicals $R^1$ to $R^5$ is methyl, ethyl or chlorine and the remaining radicals $R^1$ to $R^5$ are each hydrogen;

$R^3$ is dimethylamino and the remaining radicals $R^1$, $R^2$, $R^4$ and $R^5$ are each hydrogen;

all radicals $R^1$ to $R^5$ are hydrogen;

$R^2$ is carboxy or carboxamide and the remaining radicals $R^1$, $R^2$, $R^4$ and $R^5$ are each hydrogen; or $R^1$ and $R^2$ or $R^2$ and $R^3$ are 1,4-buta-1,3-dienylene and the remaining radicals $R^1$, $R^3$, $R^4$ and $R^5$ are each hydrogen;

and in particular those in which $R^1$ to $R^5$ are each hydrogen; or one of the radicals $R^1$ to $R^5$ is methyl or ethyl and the remaining radicals $R^1$ to $R^5$ are each hydrogen.

Particularly preferred pyridinium ions (IVa) are pyridinium, 2-methylpyridinium, 2-ethylpyridinium, 5-ethyl-2-methylpyridinium and 2-methyl-3-ethylpyridinium and also 1-methylpyridinium, 1-ethylpyridinium, 1-(1-butyl)pyridinium, 1-(1-hexyl)pyridinium, 1-(1-octyl)pyridinium, 1-(1-hexyl)pyridinium, 1-(1-octyl)pyridinium, 1-(1-dodecyl)-pyridinium, 1-(1-tetradecyl)pyridinium, t-(1-hexadecyl)pyridinium, 1,2-dimethyl-pyridinium, 1-ethyl-2-methylpyridinium, 1-(1-butyl)-2-methylpyridinium, 1-(1-hexyl)-2-methylpyridinium, 1-(1-octyl)-2-methylpyridinium, 1-(1-dodecyl)-2-methylpyridinium, 1-(1-tetradecyl)-2-methylpyridinium, 1-(1-hexadecyl)-2-methylpyridinium, 1-methyl-2-ethylpyridinium, 1,2-diethylpyridinium, 1-(1-butyl)-2-ethylpyridinium, 1-(1-hexyl)-2-ethylpyridinium, 1-(1-octyl)-2-ethylpyridinium, 1-(1-dodecyl)-2-ethylpyridinium, 9-(1-tetradecyl)-2-ethylpyridinium, 1-(1-hexadecyl)-2-ethylpyridinium, 1,2-dimethyl-5-ethylpyridinium, 1,5-diethyl-2-methylpyridinium, 1-(1-butyl)-2-methyl-3-ethyl-pyridinium, 1-(1-hexyl)-2-methyl-3-ethylpyridinium and 1-(1-octyl)-2-methyl-3-ethyl-pyridinium, 1-(1-dodecyl)-2-methyl-3-ethylpyridinium, 1-(1-tetradecyl)-2-methyl-3-ethyl-pyridinium and 1-(1-hexadecyl)-2-methyl-3-ethylpyridinium.

Particularly preferred pyridazinium ions (IVb) are those in which
the radicals $R^1$ to $R^4$ are each hydrogen or
one of the radicals $R^1$ to $R^4$ is methyl or ethyl and the remaining radicals $R^1$ to $R^4$ are each hydrogen.

Particularly preferred pyrimidinium ions (IVc) are those in which
$R^1$ is hydrogen, methyl or ethyl and $R^2$ to $R^4$ are each, independently of one another, hydrogen or methyl, or
$R^1$ is hydrogen, methyl or ethyl and $R^2$ and $R^4$ are each methyl and $R^3$ is hydrogen.

Particularly preferred pyrazinium ions (IVd) are those in which
$R^1$ is hydrogen, methyl or ethyl and $R^2$ to $R^4$ are each, independently of one another, hydrogen or methyl, or
$R^1$ is hydrogen, methyl or ethyl and $R^2$ and $R^4$ are each methyl and $R^3$ is hydrogen, or
$R^1$ to $R^4$ are each methyl or
$R^1$ to $R^4$ are each hydrogen.

Particularly preferred imidazolium ions (IVe) are those in which
$R^1$ is hydrogen, methyl, ethyl, 1-propyl, 1-butyl, 1-pentyl, 1-hexyl, 1-octyl, 2-hydroxyethyl or 2-cyanoethyl and $R^2$ to $R^4$ are each, independently of one another, hydrogen, methyl or ethyl.

Particularly useful imidazolium ions (IVe) are 1-methylimidazolium, 1-ethylimidazolium, 1-(1-propyl)imidazolium, 1-(1-allyl)imidazolium, 1-(1-butyl)imidazolium, 1-(1-octyl)-imidazolium, 1-(1-dodecyl)imidazolium, 1-(1-tetradecyl)imidazolium, 1-(1-hexadecyl)-imidazolium, 1,3-dimethylimidazolium, 1,3-diethylimidazolium, 1-ethyl-3-methyl-imidazolium, 1-(1-butyl)-3-methylimidazolium, 1-(1-butyl)-3-ethylimidazolium, 1-(1-hexyl)-3-methylimidazolium, 1-(1-hexyl)-3-ethylimidazolium, 1-(1-hexyl)-3-butyl-imidazolium, 1-(1-octyl)-3-methylimidazolium, 1-(1-octyl)-3-ethylimidazolium, 1-(1-octyl)-3-butylimidazolium, 1-(1-dodecyl)-3-methylimidazolium, 1-(1-dodecyl)-3-ethylimidazolium, 1-(1-dodecyl)-3-butylimidazolium, 1-(1-dodecyl)-3-octylimidazolium, 1-(1-tetradecyl)-3-methylimidazolium, 1-(1-tetradecyl)-3-ethylimidazolium, 1-(1-tetradecyl)-3-butylimidazolium, 1-(1-tetradecyl)-3-octylimidazolium, 1-(1-hexadecyl)-3-methylimidazolium, 1-(1-hexadecyl)-3-ethylimidazolium, 1-(1-hexadecyl)-3-butylimidazolium, 1-(1-hexadecyl)-3-octylimidazolium, 1,2-dimethyl-imidazolium, 1,2,3-trimethylimidazolium, 1-ethyl-2,3-dimethylimidazolium, 1-(1-butyl)-2,3-dimethylimidazolium, 1-(1-hexyl)-2,3-dimethylimidazolium, 1-(1-octyl)-2,3-dimethyl-imidazolium, 1,4-dimethylimidazolium, 1,3,4-trimethylimidazolium, 1,4-dimethyl-3-ethyl-imidazolium, 3-methylimidazolium, 3-ethylimidazolium, 3-n-propylimidazolium, 3-n-butylimidazolium, 1,4-dimethyl-3-octylimidazolium, 1,4,5-trimethylimidazolium, 1,3,4,5-tetramethylimidazolium, 1,4,5-trimethyl-3-ethylimidazolium, 1,4,5-trimethyl-3-butylimidazolium, 1,4,5-trimethyl-3-octylimidazolium, 1-(prop-1-en-3-yl)-3-methylimidazolium and 1-(prop-1-en-3-yl)-3-butylimidazolium. Especially suitable imidazolium ions (IVe) are 1,3-diethylimidazolium, 1-ethyl-3-methylimidazolium, 1-(n-butyl)-3-methylimidazolium.

Particularly preferred pyrazolium ions (IVf), (IVg) and (IVg') are those in which $R^1$ is hydrogen, methyl or ethyl and $R^2$ to $R^4$ are each, independently of one another, hydrogen or methyl.

Particularly preferred pyrazolium ions (IVh) are those in which
$R^1$ to $R^4$ are each, independently of one another, hydrogen or methyl.

As particularly preferred pyrazolium ions, mention may be made of pyrazolium and 1,4-dimethylpyrazolium.

1-Pyrazolinium ions (IVi) used in the process of the invention are particularly preferably those in which
$R^1$ to $R^6$ are each, independently of one another, hydrogen or methyl.

Particularly preferred 2-pyrazolinium ions (IVj) and (IVj') are those in which $R^1$ is hydrogen, methyl, ethyl or phenyl and $R^2$ to $R^6$ are each, independently of one another, hydrogen or methyl.

Particularly preferred 3-pyrazolinium ions (IVk) and (IVk') are those in which $R^1$ and $R^2$ are each, independently of one another, hydrogen, methyl, ethyl or phenyl and $R^3$ to $R^6$ are each, independently of one another, hydrogen or methyl.

Particularly preferred imidazolinium ions (IV l) are those in which $R^1$ and $R^2$ are each, independently of one another, hydrogen, methyl, ethyl, 1-butyl or phenyl and $R^3$ and $R^4$ are each, independently of one another, hydrogen, methyl or ethyl and $R^5$ and $R^6$ are each, independently of one another, hydrogen or methyl.

Particularly preferred imidazolinium ions (IVm) and (IVm') are those in which $R^1$ and $R^2$ are each, independently of one another, hydrogen, methyl or ethyl and $R^3$ to $R^6$ are each, independently of one another, hydrogen or methyl.

Particularly preferred imidazolinium ions (IVn) and (IVn') are those in which $R^1$ to $R^3$ are each, independently of one another, hydrogen, methyl or ethyl and $R^4$ to $R^6$ are each, independently of one another, hydrogen or methyl.

Particularly preferred thiazolium ions (IVo) and (IVo') and oxazolium ions (IVp) are those in which
$R^1$ is hydrogen, methyl, ethyl or phenyl and $R^2$ and $R^3$ are each, independently of one another, hydrogen or methyl.

1,2,4-Triazolium ions (IVq), (IVq') and (IVq") used in the process of the invention are particularly preferably those in which
$R^1$ and $R^2$ are each, independently of one another, hydrogen, methyl, ethyl or phenyl and $R^3$ is hydrogen, methyl or phenyl.

Particularly preferred 1,2,3-triazolium ions (IVr), (IVr') and (IVr") are those in which $R^1$ is hydrogen, methyl or ethyl, $R^2$ and $R^3$ are each, independently of one another, hydrogen or methyl or $R^2$ and $R^3$ are together 1,4-buta-1,3-dienylene.

Particularly preferred pyrrolidinium ions (IVs) are those in which $R^1$ is hydrogen, methyl, ethyl or phenyl and $R^2$ to $R^9$ are each, independently of one another, hydrogen or methyl.

Particularly preferred imidazolidinium ions (IVt) are those in which $R^1$ and $R^4$ are each, independently of one another, hydrogen, methyl, ethyl or phenyl and $R^2$, $R^3$ and $R^5$ to $R^8$ are each, independently of one another, hydrogen or methyl.

Particularly preferred ammonium ions (IVu) are those in which
$R^1$ to $R^3$ are each, independently of one another, $C_1$-$C_{18}$-alkyl, or
$R^1$ and $R^2$ are together 1,5-pentylene or 3-oxa-1,5-pentylene and $R^3$ is selected from among $C_1$-$C_{18}$-alkyl, 2-hydroxyethyl and 2-cyanoethyl.

Examples of tertiary amines from which the quaternary ammonium ions of the general formula (IVu) are derived by quaternization with the abovementioned radical R are diethyl-n-butylamine, diethyl-tert-butylamine, diethyl-n-pentylamine, diethylhexylamine, diethyloctylamine, diethyl-(2-ethylhexyl)amine, di-n-propylbutylamine, di-n-propyl-n-pentylamine, di-n-propylhexylamine, di-n-propyloctylamine, di-n-propyl-(2-ethylhexyl)-amine, diisopropylethylamine, diisopropyl-n-propylamine, diisopropylbutylamine, diisopropylpentylamine, diisopropylhexylamine, diisopropyloctylamine, diisopropyl-(2-ethylhexyl)amine, di-n-butylethylamine, di-n-butyl-n-propylamine, di-n-butyl-n-pentyl-amine, di-n-butylhexylamine, di-n-butyloctylamine, di-n-butyl-(2-ethylhexyl)amine, N-n-butylpyrrolidine, N-sec-butylpyrrolidine, N-tert-butylpyrrolidine, N-n-pentylpyrrolidine, N,N-dimethylcyclohexylamine, N,N-diethylcyclohexylamine, N,N-di-n-butylcyclohexylamine, N-n-propylpiperidine, N-isopropylpiperidine, N-n-butyl-piperidine, N-sec-butylpiperidine, N-tert-butylpiperidine, N-n-pentylpiperidine, N-n-butylmorpholine, N-sec-butylmorpholine, N-tert-butylmorpholine, N-n-pentyl-morpholine, N-benzyl-n-ethylaniline, N-benzyl-N-n-propylaniline, N-benzyl-N-isopropyl-aniline, N-benzyl-N-n-butylaniline, N,N-dimethyl-p-toluidine, N,N-diethyl-p-toluidine, N,N-di-n-butyl-p-toluidine, diethylbenzylamine, di-n-propylbenzylamine, di-n-butyl-benzylamine, diethylphenylamine, di-n-propylphenylamine and di-n-butylphenylamine.

Preferred tertiary amines (IVu) are diisopropylethylamine, diethyl-tert-butylamine, diisopropylbutylamine, di-n-butyl-n-pentylamine, N,N-di-n-butylcyclohexylamine and also tertiary amines derived from pentylisomers.

Particularly preferred tertiary amines are di-n-butyl-n-pentylamine and tertiary amines derived from pentyl isomers. A further preferred tertiary amine which has three identical radicals is triallylamine.

Particularly preferred guanidinium ions (IVv) are those in which $R^1$ to $R^5$ are each methyl. As a very particularly preferred guanidinium ion (IVv), mention may be made of N,N,N',N',N'',N''-hexamethylguanidinium.

Particularly preferred cholinium ions (IVw) are those in which $R^1$ and $R^2$ are each, independently of one another, methyl, ethyl, 1-butyl or 1-octyl and $R^3$ is hydrogen, methyl, ethyl, acetyl, —SO$_2$OH or —PO(OH)$_2$, or $R^1$ is methyl, ethyl, 1-butyl or 1-octyl, $R^2$ is a —CH$_2$_CH$_2$_OR$^4$ group and $R^3$ and $R^4$ are each, independently of one another, hydrogen, methyl, ethyl, acetyl, —SO$_2$OH or —PO(OH)$_2$, or $R^1$ is a —CH$_2$_CH$_2$_OR$^4$ group, $R^2$ is a —CH$_2$_CH$_2$_OR$^5$ group and $R^3$ to $R^5$ are each, independently of one another, hydrogen, methyl, ethyl, acetyl, —SO$_2$OH or —PO(OH)$_2$.

As cholinium ions (IVw), particular preference is given to those in which $R^3$ is selected from among hydrogen, methyl, ethyl, acetyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxa-tetradecyl.

The cations (IV.x.1) are particularly preferably selected from among cations of 1,5-diazabicyclo[4.3.0]non-5-ene (DBN) and 1,8-diazabicyclo[5.4.0]undec-7-ene (DBU).

Particularly preferred phosphonium ions (IVy) are those in which $R^1$ to $R^3$ are each, independently of one another, C$_1$-C$_{18}$-alkyl, in particular butyl, isobutyl, 1-hexyl or 1-octyl, or phenyl which is unsubstituted or bears 1, 2, 3, 4 or 5 substituents selected independently from among C$_1$-C$_{18}$-alkyl, carboxylate, sulfonate, COOH and SO$_3$H.

Particularly preferred sulfonium ions (IVz) are those in which $R^1$ and $R^2$ are each, independently of one another, C$_1$-C$_{18}$-alkyl, in particular butyl, isobutyl, 1-hexyl or 1-octyl.

Among the abovementioned heterocyclic cations, the imidazolium ions, imidazolinium ions, pyridinium ions, pyrazolinium ions and pyrazolium ions are preferred. Particular preference is given to the imidazolium ions and also cations of DBU and DBN.

As anions, it is in principle possible to use all polyatomic anions, i.e. multiatomic anions (anions having two or more than two atoms).

The anion $[Y]^{n-}$ of the ionic liquid is, for example, selected from the group of pseudohalides and halogen-comprising compounds of the formulae:

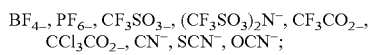

the group of sulfates, sulfites and sulfonates of the general formulae:

the group of phosphates of the general formulae:

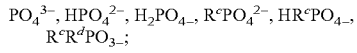

the group of phosphonates and phosphinates of the general formulae:

the group of phosphites of the general formulae:

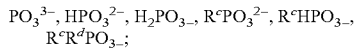

the group of phosphonites and phosphinites of the general formulae:

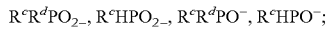

the group of carboxylic acids of the general formula:

anions of hydroxycarboxylic acids and sugar acids;
saccharinates (salts of o-benzosulfimide);
the group of borates of the general formulae:

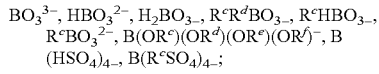

the group of boronates of the general formulae:

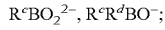

the group of carbonates and carboxylic esters of the general formulae:

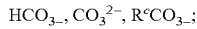

the group of silicates and silicic esters of the general formulae:

the group of alkylsilanolates and arylsilanolates of the general formulae:

the group of carboximides, bis(sulfonyl)imides and sulfonylimides of the general formulae:

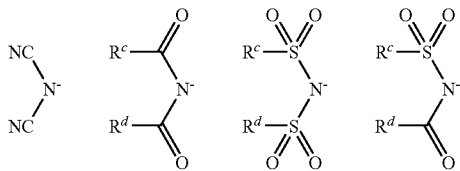

the group of methides of the general formula:

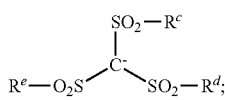

the group of alkoxides and aryloxides of the general formula $R^cO^-$;
the group of hydrogensulfides, polysulfides, hydrogenpolysulfides and thiolates of the general formulae:

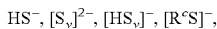

where v is a positive integer from 2 to 10.

Preference is given to the radicals $R^c$, $R^d$, $R^e$ and $R^f$ each being, independently of one another,
hydrogen;
alkyl, preferably $C_1$-$C_{30}$-alkyl, particularly preferably $C_1$-$C_{18}$-alkyl, which is unsubstituted or substituted as defined above and/or may, as defined above, be interrupted by at least one heteroatom or heteroatom-comprising group;
aryl, preferably $C_6$-$C_{14}$-aryl, particularly preferably $C_6$-$C_{10}$-aryl, which is unsubstituted or substituted as defined above;
cycloalkyl, preferably $C_5$-$C_{12}$-cycloalkyl, which is unsubstituted or substituted as defined above;
heterocycloalkyl, preferably heterocycloalkyl having 5 or 6 ring atoms, where the ring has, apart from ring carbons, 1, 2 or 3 heteroatoms or heteroatom-comprising groups and is unsubstituted or substituted as defined above; heteroaryl, preferably heteroaryl having from 5 to 10 ring atoms, where the ring has, apart from ring carbons, 1, 2 or 3 heteroatoms or heteroatom-comprising groups selected from among oxygen, nitrogen, sulfur and $NR^a$ and is unsubstituted or substituted as defined above;
where, in anions which have a plurality of radicals $R^c$ to $R^f$, two of these radicals together with the part of the anion to which they are bound can also form at least one saturated, unsaturated or aromatic ring or ring system having from 1 to 12 carbon atoms, where the ring or ring system can have from 1 to 5 nonadjacent heteroatoms or heteroatom-comprising groups which are preferably selected from among oxygen, nitrogen, sulfur and $NR^a$ and the ring or the ring system is unsubstituted or can be substituted.

As regards suitable and preferred $C_1$-$C_{30}$-alkyls, in particular $C_1$-$C_{18}$-alkyls, $C_6$-$C_{14}$-aryls, in particular $C_6$-$C_{10}$-aryls, $C_5$-$C_{12}$-cycloalkyls, heterocycloalkyls having 5 or 6 ring atoms and heteroaryls having 5 or 6 ring atoms, what has been said above applies. As regards suitable and preferred substituents on $C_1$-$C_{30}$-alkyl, especially $C_1$-$C_{18}$-alkyl, $C_6$-$C_{14}$-aryl, $C_5$-$C_{12}$-cycloalkyl, heterocycloalkyl having 5 or 6 ring atoms and heteroaryl having 5 or 6 ring atoms, what has been said above with regard to substituents likewise applies.

If at least one of the radicals $R^c$ to $R^f$ is optionally substituted $C_1$-$C_{14}$-alkyl, then it is preferably methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hetadecyl, octadecyl, 1,1-dimethylpropyl, 1,1-dimethylbutyl, 1,1,3,3-tetramethylbutyl, benzyl, 1-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonyl-propyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, trichloromethyl, trifluoromethyl, 1,1-dimethyl-2-chloro-ethyl, 2-methoxyisopropyl, 2-ethoxyethyl, butylthiomethyl, 2-dodecylthioethyl, 2-phenyl-thioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 4-aminobutyl, 6-amino-hexyl, 2-methylaminoethyl, 2-methylaminopropyl, 3-methylaminopropyl, 4-methyl-aminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl.

If at least one of the radicals $R^c$ to $R^f$ is $C_1$-$C_{18}$-alkyl interrupted by one or more nonadjacent heteroatoms or heteroatom-comprising groups, then it is preferably 5-hydroxy-3-oxapentyl, 8-hydroxy-3,6-dioxaoctyl, 11-hydroxy-3,6,9-trioxaundecyl, 7-hydroxy-4-oxaheptyl, 11-hydroxy-4,8-dioxaundecyl, 15-hydroxy-4,8,12-trioxa-pentadecyl, 9-hydroxy-5-oxanonyl, 14-hydroxy-5,10-oxatetradecyl, 5-methoxy-3-oxa-pentyl, 8-methoxy-3,6-dioxaoctyl, 11-methoxy-3,6,9-trioxaundecyl, 7-methoxy-4-oxa-heptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxa-octyl, 11-ethoxy-3,6,9-trioxaundecyl, 7-ethoxy-4-oxaheptyl, 11-ethoxy-4,8-dioxa-undecyl, 15-ethoxy-4,8,12-trioxapentadecyl, 9-ethoxy-5-oxanonyl or 14-ethoxy-5,10-oxatetradecyl.

If two radicals $R^c$ to $R^f$ form a ring, then these radicals can together form as fused-on building block, for example, 1,3-propylene, 1,4-butylene, 2-oxa-1,3-propylene, 1-oxa-1,3-propylene, 2-oxa-1,3-propenylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

The number of nonadjacent heteroatoms or heteroatom-comprising groups of the radicals $R^c$ to $R^f$ is in principle not critical and is generally restricted only by the size of the respective radical or ring building block. In general, there will be no more than 5 in the respective radical, preferably no more than 4 and very particularly preferably no more than 3. Furthermore, there is generally at least one carbon atom, preferably at least two carbon atoms, between any two heteroatoms.

Substituted and unsubstituted imino groups can be, for example, imino, methylimino, isopropylimino, n-butylimino or tert-butylimino.

Preferred functional groups of the radicals $R^c$ to $R^f$ are carboxy, carboxamide, hydroxy, di($C_1$-$C_4$-alkyl)amino, $C_1$-$C_4$-alkyloxycarbonyl, cyano or $C_1$-$C_4$-alkoxy. Radicals $R^c$ to $R^f$ other than alkyl may additionally be substituted by one or more $C_1$-$C_4$-alkyl groups, preferably methyl, ethyl, propyl, isopropyl, n-butyl, sec-butyl or tert-butyl.

If at least one of the radicals $R^c$ to $R^f$ is optionally substituted $C_6$-$C_{14}$-aryl, then it is preferably phenyl, methylphenyl (tolyl), xylyl, a-naphthyl, 3-naphthyl, chlorophenyl, dichlorophenyl, trichlorophenyl, difluorophenyl, dimethylphenyl, trimethylphenyl, ethyl-phenyl, diethylphenyl, isopropylphenyl, tert-butylphenyl, dodecylphenyl, methoxy-phenyl, dimethoxyphenyl, ethoxyphenyl, hexyloxyphenyl, methyl-naphthyl, isopropyl-naphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl.

If at least one of the radicals $R^c$ to $R^f$ is optionally substituted $C_5$-$C_{12}$-cycloalkyl, then it is preferably cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl or a saturated or unsaturated bicyclic system such as norbornyl or norbornenyl.

If at least one of the radicals $R^c$ to $R^f$ is an optionally substituted five- or six-membered heterocycle, then it is preferably furyl, thienyl, pyryl, pyridyl, indolyl, benzoxazolyl, dioxolyl, dioxyl, benzimidazolyl, benzthiazolyl, dimethylpyridyl, methylquinolyl, dimethylpyryl, methoxifuryl, dimethoxypyridyl, difluoropyridyl, methylthiophenyl, isopropylthiophenyl or tert-butylthiophenyl.

If, in anions which have a plurality of radicals $R^c$ to $R^f$, two of these radicals together with the part of the anion to which they are bound can also form at least one saturated, unsaturated or aromatic ring or ring system having from 1 to 12 carbon atoms, where the ring or the ring system can have from 1 to 5 nonadjacent heteroatoms or heteroatom-comprising groups which are preferably selected from among oxygen, nitrogen, sulfur and $NR^a$, then the ring or the ring system is unsubstituted or bears 1, 2, 3, 4, 5 or more than 5 substituents. The substituents are preferably selected independently from among alkyl, alkoxy, alkylsulfanyl, cycloalkyl, cycloalkoxy, polycyclyl, heterocycloalkyl, aryl, aryloxy, arylthio and heteroaryl.

Preferred anions are, for example, selected from the group of pseudohalides and halogen-comprising compounds, the group of carboxylic acids, the group of sulfates, sulfites and sulfonates and the group of phosphates.

Preferred anions are formate, acetate, propionate, butyrate, lactate, saccharinate, carbonate, hydrogencarbonate, sulfate, sulfite, $C_1$-$C_4$-alkylsulfates, methanesulfonate, tosylate, trifluoroacetate, $C_1$-$C_4$-dialkylphosphates and hydrogensulfate.

Particularly preferred anions are HCOO—, $CH_3$COO—, $CH_3CH_2$COO—, carbonate, hydrogencarbonate, sulfate, sulfite, tosylate, $CH_3SO_{3-}$ or $CH_3OSO_{3-}$.

Suitable ionic liquids for use in the process of the invention are commercially available, e.g. under the trade name Basionic® from BASF Aktiengesellschaft. Commercial ionic liquids which are advantageous for use in the process of the invention are, for example:

1-ethyl-3-methylimidazolium methanesulfonate (EMIM $CH_3SO_3$, Basionic ST 35),
1-butyl-3-methylimidazolium methanesulfonate (BMIM $CH_3SO_3$, Basionic ST 78),
methylimidazolium hydrogensulfate (HMIM $HSO_4$, Basionic AC 39),
1-butyl-3-methylimidazolium hydrogensulfate (BMIM $HSO_4$, Basionic AC 28)1-ethyl-3
methylimidazolium hydrogensulfate (EMIM $HSO_4$, Basionic AC 25),
1-ethyl-3-methylimidazolium acetate (EMIM acetate, Basionic BC 01),
1-butyl-3-methylimidazolium acetate (BMIM acetate, Basionic BC 02).

Particular preference is given to 1-ethyl-3-methylimidazolium acetate, 1,3-diethylimidazolium acetate and 1-butyl-3-methylimidazolium acetate. Cations and anions are present in the ionic liquid. Within the ionic liquid, a proton or an alkyl radical is transferred from the cation to the anion. This forms two uncharged molecules. There is therefore an equilibrium in which anions, cations and the two uncharged molecules formed therefrom are present.

As cellulose, it is possible to use any known form of cellulose, e.g. from wood fibers, linters, pulp, copper, cellulose obtained from paper, regenerated cellulose or bacterial cellulose. Preferred cellulose-comprising starting materials for use in the process of the invention are those mentioned above, i.e. cellulose, cellulose-comprising paper materials and cellulose-rich natural fibers such as flax, hemp, sisal, jute, straw, coconut fibers, switchgrass (*Panicum virgatum*) and other natural fibers. If pure cellulose is not used, it can be advantageous to subject the cellulose-comprising starting material to at least one pretreatment step before treatment with the ionic liquid. Such steps include, for example, mechanical comminution of the cellulose-comprising starting material, e.g. by milling and/or shredding. These further components include, inter alia, hemicelluloses or polyoses which, like cellulose, are made up of glycosidically linked sugar units but the chains are more or less branched and the degree of polymerization is lower than that of cellulose (in general from about 50 to 250). Since hemicellulose is in principle likewise capable of enzymatic degradation, the cellulose-comprising starting material used in the process of the invention can also comprise hemicellulose. The treatment of the cellulose-comprising starting material with the ionic liquid is generally carried out by bringing the cellulose material into intimate contact with the ionic liquid. Here, at least the cellulose comprised in the cellulose-comprising starting material is dissolved in the treatment medium comprising the ionic liquid. The cellulose material is preferably completely dissolved in the treatment medium comprising the ionic liquid. If necessary, the cellulose material is subjected beforehand to a pretreatment step to remove insoluble constituents or insoluble constituents are separated off from the treatment medium. To produce a solution, the cellulose material and the ionic liquid can be mechanically mixed and stirred until complete dissolution has occurred.

The process of the invention advantageously makes it possible to treat relatively concentrated solutions of the cellulose material in the ionic liquid. The solution used for the treatment preferably has a cellulose content, based on dissolved cellulose and ionic liquid, of at least 1% by weight, particularly preferably at least 5% by weight, in particular at least 7% by weight. The solution generally has a cellulose content, based on dissolved cellulose and ionic liquid, of not more than 50% by weight, for example not more than 35% by weight.

The process of the invention preferably comprises the treatment of the cellulose material with at least one ionic liquid as defined above at a temperature of not more than 200° C., particularly preferably not more than 150° C. and in particular not more than 120° C. The treatment is preferably carried out at a temperature of at least 20° C., particularly preferably at least 40° C., in particular at least 60° C. Heating can be effected either indirectly or directly, preferably indirectly. For direct heating, it is possible to use a hot heat transfer fluid which is compatible with the ionic liquid used. Indirect heating can be carried out using apparatuses customary for this purpose, e.g. by means of heat exchangers, heating baths or microwave radiation.

The pressure in the treatment of the cellulose material with at least one ionic liquid is generally in the range from 0.1 bar to 100 bar, preferably from 1 bar to 10 bar. In a specific embodiment, the treatment is carried out at ambient pressure.

The duration of the treatment of the cellulose material with the ionic liquid is generally from 0.5 minutes to 5 days, preferably from 1 minute to 24 hours, especially from 5 minutes to 10 hours.

The process of the invention advantageously makes it possible to treat the cellulose-comprising starting material with an ionic liquid which comprises water in an amount which does not yet result in precipitation of the cellulose from the treatment medium. The water can, for example, originate from the cellulose-comprising starting material or have been present in the ionic liquid. The tolerance of the ionic liquids based on polyatomic anions which are used according to the invention toward water represents a significant simplification of the process since the additional engineering outlay associated with working in the absence of water, e.g. for treatment of the cellulose under a protective gas atmosphere, complicated drying of recovered ionic liquid to remove traces of water, etc., is not necessary.

The water content of the liquid treatment medium is preferably from 0.1 to 15% by weight, particularly preferably from 0.5 to 10% by weight, in particular from 1 to 8% by weight, based on the weight of the total treatment liquid (ionic liquid, water and possibly further components which are liquid under the treatment conditions). It is naturally also possible to carry out the treatment at water contents below 0.5% by weight, since the lower limit to the water content is not critical for the in-principle performance of the process, whereas water contents which are too high result in precipitation of the cellulose. The water can originate from the ionic liquid used (for example water which has not been separated off from recirculated ionic liquid after the precipitation of the cellulose) and/or from the cellulose material used.

The liquid treatment medium can comprise at least one organic solvent in place of or in addition to water. Suitable organic solvents are those described below as precipitants. The organic solvent content of the treatment medium is preferably not more than 15% by weight, in particular not more than 10% by weight, especially not more than 5% by weight, based on the total weight of the liquid treatment medium. In a specific embodiment, the treatment medium is substantially free of organic solvents.

The cellulose material which has been treated with the ionic liquid is preferably isolated prior to the enzymatic hydrolysis. The isolation is generally effected by addition of a precipitant and subsequent separation into a fraction comprising precipitated cellulose and a liquid fraction (i.e. a first liquid discharge (A1)).

The precipitation of the cellulose is preferably carried out using a solvent or solvent mixture (precipitant) selected from among water, alcohols such as methanol, ethanol, n-propanol, isopropanol, n-butanol, tert-butanol, diols and polyols such as ethanediol and propanediol, amino alcohols such as ethanolamine, diethanolamine and triethanolamine, aromatic solvents, e.g. benzene, toluene, ethylbenzene or xylenes, halogenated solvents, e.g. dichloromethane, chloroform, carbon tetrachloride, dichloroethane or chlorobenzene, aliphatic solvents, e.g. pentane, hexane, heptane, octane, ligroin, petroleum ether, cyclohexane and decalin, ethers, e.g. tetrahydrofuran, diethyl ether, methyl tert-butyl ether and diethylene glycol monomethyl ether, ketones such as acetone and methyl ethyl ketone, esters, e.g. ethyl acetate, and mixtures thereof. The precipitant is preferably selected from among water, water-miscible organic solvents and mixtures thereof. Preferred water-miscible organic solvents are the abovementioned alcohols, in particular methanol and/or ethanol. In a first preferred embodiment, a water-comprising medium is used as precipitant. Suitable water-comprising media are water and mixtures of water and at least one water-miscible precipitant different therefrom. Particular preference is given to using water or a water/alcohol mixture as precipitant. In a second preferred embodiment, an organic solvent is used as precipitant. Preference is given to the abovementioned alcohols, in particular methanol and/or ethanol.

The precipitants can further comprise ionic liquids. The proportion of ionic liquid in the precipitant will generally be not more than 50% by weight, based on the total weight of the precipitant. Such a content of ionic liquids is not critical to the success of the cellulose precipitation. This ionic liquid comprised in the precipitant can, for example, originate from a use of recovered precipitant for the after-treatment of the precipitated cellulose in order to remove residual amounts of ionic liquid still comprised therein, as is described below.

The separation into a fraction comprising precipitated cellulose and a liquid fraction (the first liquid discharge (A1)) is carried out by, for example, filtration. To accelerate the filtration, it can be carried out under increased pressure on the cellulose side or reduced pressure on the outflow side. Likewise, the separation can be effected by centrifugation. Customary centrifugation methods are described, for example, in G. Hultsch, H. Wilkesmann, "Filtering Centrifuges," in D. B. Purchas, Solid-Liquid Separation, Upland Press, Croydon 1977, pp. 493-559; and H. Trawinski in "Die äquivalente Klärfläche von Zentrifugen", Chem. Ztg. 83 (1959), 606-612. Various construction types such as tube centrifuges and basket centrifuges and also especially pusher centrifuges, invertible filter centrifuges and plate separators can be used.

The liquid discharge (A1) which is obtained in the separation and comprises ionic liquid and precipitant is preferably subjected to a further separation into a fraction (IL1) comprising essentially the ionic liquid and a fraction (F1) comprising essentially the precipitant. This separation is generally effected by vaporization of the precipitant, e.g. by distillation. Suitable separation apparatuses are the distillation columns and vaporizers customary for this purpose, e.g. falling film evaporators, forced circulation depressurization evaporators, short path evaporators or thin film evaporators. Owing to the low volatility of the ionic liquid, complicated apparatuses as are used in the separation of mixtures having boiling points which are close together, e.g. complicated column internals, columns having a large number of theoretical plates, etc., can generally be dispensed with. When water is used as precipitant, it is not necessary to subject the fraction comprising the ionic liquid to additional drying because of the above-described tolerance of the ionic liquids used according to the invention toward water.

The separation of the liquid fraction into a fraction (IL1) comprising essentially the ionic liquid and a fraction (F1)

comprising essentially the precipitant generally enables at least 80% by weight, particularly preferably at least 90% by weight, in particular at least 93% by weight, of the ionic liquid used in the treatment of the cellulose-comprising starting material to be recovered. The fraction (IL1) comprising essentially the ionic liquid is preferably reused for treatment of the cellulose-comprising starting material.

The fraction comprising essentially the precipitant can be reused for precipitation of the cellulose after the treatment of the cellulose-comprising starting material. This is the case especially when a water-miscible organic solvent, e.g. an alcohol, is used as precipitant. As an alternative, the fraction comprising essentially the precipitant can be used for treatment of the precipitated cellulose in order to free it of ionic liquid still comprised. This is the case especially when an aqueous medium, in particular water, is used as precipitant.

The precipitated cellulose is preferably subjected to a treatment to remove ionic liquid still comprised. For this purpose, the cellulose can, for example, be subjected to washing with a liquid washing medium. Suitable washing media are ones in which the ionic liquid readily dissolves and cellulose does not dissolve or dissolves only in small amounts. Preferred washing media are the above-described precipitants. The washing medium is particularly preferably selected from among water and mixtures of water and at least one water-miscible solvent different therefrom. Particular preference is given to using water as washing medium.

The treatment of the cellulose with a washing medium is preferably carried out at elevated temperature. This is preferably at or below the boiling point of the washing medium. The treatment of the cellulose with a washing medium is preferably carried out at a temperature of at least 40° C., particularly preferably at least 60° C., in particular at least 80° C. When water is used as washing medium, the treatment of the cellulose is preferably carried out at a temperature of at least 80° C., particularly preferably at least 90° C., in particular at least 95° C.

To remove the ionic liquid comprised, the precipitated cellulose can be subjected once or a number of times in succession to a treatment with a washing medium. For this purpose, the cellulose is brought into intimate contact with the washing medium in a suitable apparatus and the washing medium is subsequently separated off from the cellulose. Suitable apparatuses are, for example, stirred vessels which, if necessary, can be provided with a heating device and a facility for condensation and recirculation of the washing medium. The separation of cellulose and washing medium is effected, for example, by filtration. To accelerate the filtration, it can be carried out under increased pressure on the cellulose side or reduced pressure on the outflow side.

As mentioned above, in a preferred embodiment, a fraction used as precipitant and obtained after separation from the precipitated cellulose and at least the major part of the ionic liquid is used for treatment of the precipitated cellulose in order to free it of ionic liquid still comprised. In this preferred embodiment, the washing medium thus comprises a precipitant fraction. The latter is obtained by precipitation of the cellulose, separation into the fraction comprising the precipitated cellulose and a fraction comprising the liquid discharge (A1) and subsequent separation of the liquid discharge (A1) into a fraction (IL1) comprising essentially the ionic liquid and a fraction (F1) comprising essentially the precipitant.

In the treatment of the precipitated cellulose to remove ionic liquid still comprised, a liquid washing medium laden with ionic liquid (the second liquid discharge (A2)) is obtained. The laden washing medium generally has an ionic liquid content of from 0.5 to 20% by weight, preferably from 1 to 10% by weight, based on the total weight of the washing medium.

The liquid discharge (A2) can be subjected to a separation into a fraction (IL2) comprising essentially the ionic liquid and a fraction comprising essentially the washing medium. The ionic liquid can then be reused for treatment of the cellulose-comprising starting material. The washing medium can likewise be reused as washing medium and/or as precipitant. If desired, the liquid discharge (A2) can for this purpose, depending on its composition, be subjected to a further separation to give at least one of the following fractions
a fraction (F2) which comprises essentially the precipitant and can, for example, be reused as precipitant,
a water-comprising fraction which can, for example, be reused as washing medium.

In a preferred embodiment, an aqueous medium is used as precipitation medium and the laden washing medium is used as precipitant for precipitation of the cellulose from the cellulose material which has been treated with the ionic liquid. In this way, both the ionic liquid and the precipitant/washing medium can be recirculated to the process of the invention without an additional separation step being required.

In a further preferred embodiment, at least one organic solvent is used as precipitation medium and the laden washing medium is subjected to a separation into
a fraction (IL2) comprising essentially the ionic liquid,
a fraction (F2) comprising essentially the precipitant and
a water-comprising fraction.

The treatment of the precipitated cellulose to remove ionic liquid still comprised is advantageous from a number of points of view. Firstly, a loss of expensive ionic liquid can be avoided in this way. Furthermore, it has been found that the removal of residual amounts of ionic liquid sometimes has a positive effect on the following enzymatic hydrolysis. Thus, the required amounts of enzyme used can be lower and/or the rate of the enzymatic hydrolysis can be higher when the precipitated cellulose comprises no ionic liquid or only small residual amounts of ionic liquid.

The treatment of the precipitated cellulose with a heated washing medium is particularly advantageous.

The cellulose material which has been treated with the ionic liquid generally comprises no or only very little crystalline material. The determination of the proportion of crystalline material can, for example, be carried out by X-ray diffraction (XRD) by means of the ratio of sharp signals to X-ray-amorphous regions.

It has surprisingly been found that cellulose which has been pretreated according to the process of the invention can be subjected to rapid enzymatic hydrolysis essentially independently of its degree of polymerization. The mean degrees of polymerization of the cellulose-comprising material used for the enzymatic hydrolysis are, for example, from 100 to 2000.

The cellulose-comprising starting material which has been treated according to the process of the invention is subsequently subjected to an enzymatic hydrolysis.

Suitable enzymes for use in the process of the invention are the cellulases belonging to the category of hydrolases (1,4-(1,3; 1,4)-β-D-glucan-4-glucanohydrolases). The EC number is 3.2.1.4., and the CAS number is 9012-54-8. The cellulase enzyme complex comprises three different types of enzyme: endoglucanases break the bonds within the cellulose in order to break up the crystalline structure, exoglucanases separate relatively small oligosaccharide units, in general disaccharide and tetrasaccharide units (cellobiose, cellotetrose units), from the ends of the relatively small chains produced by the endoglucanase. Cellobiases or β-glucosidases cleave the bond between the glucose molecules in the oligosaccharides. Suitable cellulases are, for example, those from *Trichoderma reesei* (ATCC#26799), which are commercially available from Worthington Biochemical Corporation. Further suitable cellulases are the cellulase mixtures Celluclast 1.5 L with Novozym 188 (Novozymes, Denmark) or Spezyme CP (Genencor International Inc., Rochester, USA) with Novozym 188 (Novozymes, Denmark).

The enzymatic hydrolysis is preferably carried out in an aqueous medium. The aqueous medium used is essentially free of ionic liquids. For the purposes of the present patent application, "essentially free of ionic liquid" means a content of less than 0.1% by volume, preferably less than 0.1% by volume, based on the total volume of the liquid reaction medium used for the hydrolysis.

The enzymatic hydrolysis is carried out at a pH suitable for the enzymes used. An advantageous pH range for many of the enzymes which can be used according to the invention is from about 4 to 5.5. Naturally, it is in individual cases also possible to work at a higher or lower pH if the enzyme used permits this. The pH can be set by means of the buffer systems which are customary for this purpose and are known to those skilled in the art. These include acetate buffers, tris buffers, etc.

The enzymatic hydrolysis is preferably carried out at a temperature of from 0 to 80° C., particularly preferably from 20 to 60° C.

In a preferred embodiment of the process of the invention, the mass flows and/or energy flows are integrated in such a way that the ionic liquid used is essentially completely recycled and/or the heat required in the process (e.g. for the separation of ionic liquid and precipitant) is at least partly used in another step of the process.

A preferred process comprises the following steps:
a) treatment of the cellulose-comprising starting material with a liquid treatment medium comprising an ionic liquid to give a solution of cellulose in the treatment medium,
b) precipitation of the cellulose from the solution obtained in step a) by addition of a precipitant,
c) separation into a fraction comprising the precipitated cellulose and a first liquid discharge (A1),
d) separation of the discharge (A1) into a fraction (IL1) comprising essentially the ionic liquid and a fraction (F1) comprising essentially the precipitant, with the fraction (IL1) comprising the ionic liquid being at least partly recirculated to step a),
e) treatment of the precipitated cellulose with a liquid washing medium to remove ionic liquid still comprised, with the washing medium comprising the fraction (F1) comprising the precipitant which is obtained in step d),
f) separation into a fraction comprising the precipitated, purified cellulose and a second liquid discharge (A2) which is at least partly recirculated as precipitant to step b),
g) use of the cellulose obtained in step f) in the enzymatic hydrolysis.

The above-described process is shown schematically in FIG. 1.

With regard to suitable and preferred embodiments of steps a) to g), reference is made to what has been said above in respect of these steps.

Preference is given to using a water-comprising medium as precipitant in step b) and as washing medium in step e). Particular preference is given to using water as precipitant in step b) and as washing medium in step e). In a preferred embodiment of the process of the invention, the precipitant used in step b) corresponds to the washing medium used in step e) and is conveyed in a liquid circuit. Here, the circulated precipitant/washing medium can, depending on the process step in which it is present at the particular time, have different compositions in respect of additional components comprised. This applies especially to the content of ionic liquid. It goes without saying that in each case only the amount of precipitant/washing medium required in the process step is used. Excess quantities of liquid are temporarily stored in suitable containers and reintroduced into the circuit at a suitable point. Losses of precipitant/washing medium due to the process are made up as required.

The treatment of the cellulose with the water-comprising precipitant/washing medium in step e) is preferably carried out at a temperature of at least 80° C., particularly preferably at least 90° C., in particular at least 95° C.

A further preferred process comprises the following steps:
a) treatment of the cellulose-comprising starting material with a liquid treatment medium comprising an ionic liquid to give a solution of cellulose in the treatment medium,
b) precipitation of the cellulose from the solution obtained in step a) by addition of a precipitant comprising at least one water-miscible organic solvent,
c) separation into a fraction comprising the precipitated cellulose and a first liquid discharge (A1),
d) separation of the discharge (A1) into a fraction (10) comprising essentially the ionic liquid and a fraction (F1) comprising essentially the precipitant, (IL1) being at least partly recirculated to step a) and (F1) being at least partly recirculated to step b),
e) treatment of the precipitated cellulose with a liquid washing medium to remove ionic liquid still comprised,
f1) separation into a fraction comprising the precipitated, purified cellulose and a second liquid discharge (A2),
f2) separation of the discharge (A2) into
    a fraction (IL2) which comprises essentially the ionic liquid and is at least partly recirculated to step a),
    a fraction (F2) which comprises essentially the precipitant and is at least partly recirculated to step b),
    a water-comprising fraction which is at least partly recirculated to step e),
g) use of the cellulose obtained in step f1) in the enzymatic hydrolysis.

Figure 2:
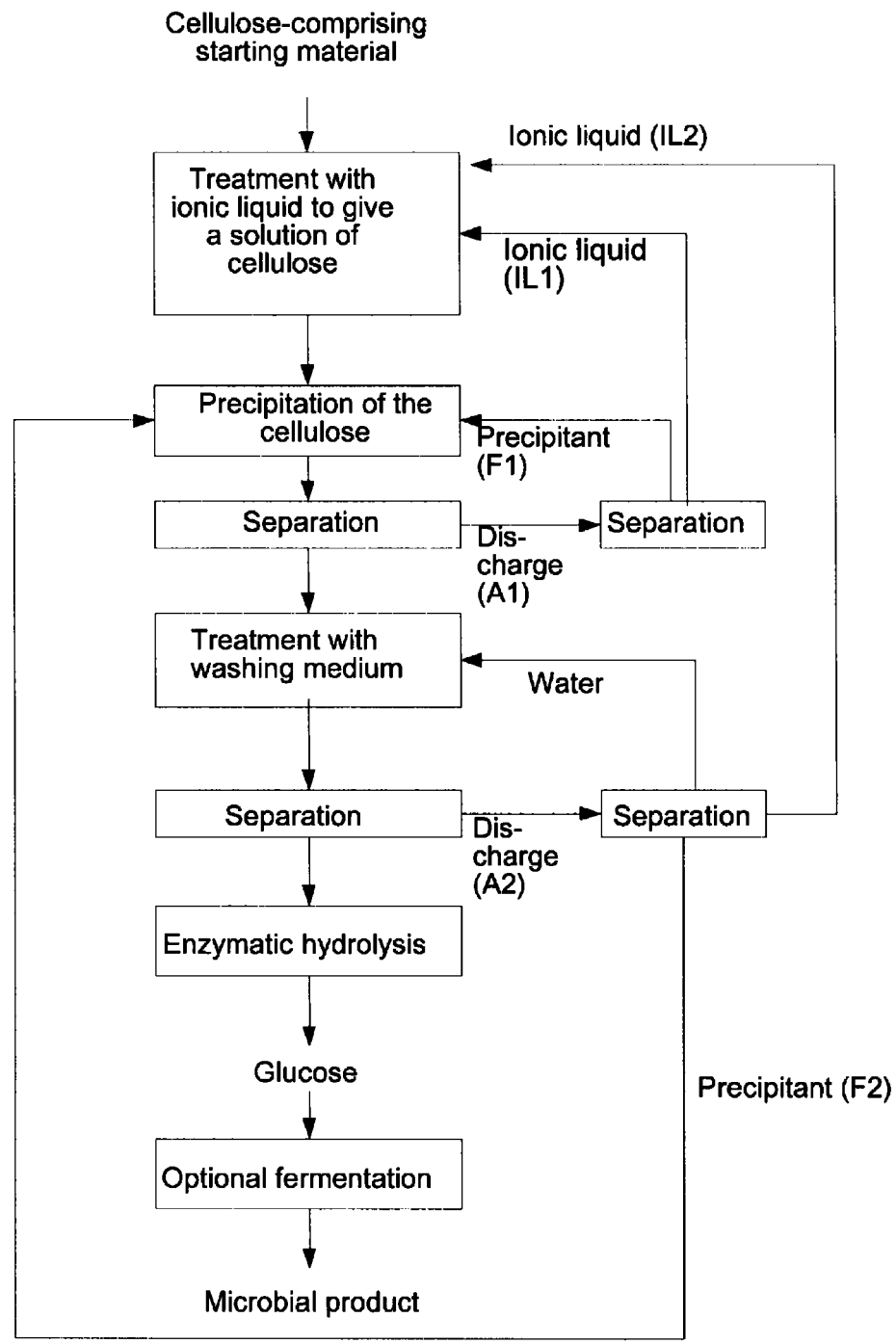

The above-described process is shown schematically in FIG. 2.

With regard to suitable and preferred embodiments of steps a) to g), reference is made to what has been said above in respect of these steps.

Shrinking petroleum reserves and increasing fuel prices are leading to growing interest in replacing petroleum-based fuels by inexpensive and environmentally friendly alternatives. Processes for producing fuels from biogenic fat- or oil-comprising starting mixtures and also used oils and animal fats have been known for a relatively long time, with rapeseed oil being predominantly used at present in central Europe as starting material in the production of biogenic fuels. Biogenic oils and fats themselves are relatively unsuitable as fuels for internal combustion engines since they have to be purified beforehand by usually complicated processes. The conversion of the triglycerides comprised in the biogenic oil and fat starting mixtures into monoalkyl esters of fatty acids, in particular methyl or ethyl esters, is known as a solution to these problems. These esters, which are also referred to as "biodiesel", can generally be used in diesel engines without major modifications. However, biodiesel is relatively expensive because of raw material prices and the refining processes required and cannot yet compete in terms of price with normal diesel fuel. A good contribution would be the use of ethanol as product from the fermentation of glucose. The invention therefore further provides a process for preparing a microbial material transformation product, in particular ethanol, which additionally comprises the step h):
h) Fermentation of the glucose obtained in step g).

Sugar-comprising liquid media are a basic starting material for many fermentation processes; the sugars comprised in the media are transformed by the microorganisms used into valuable organic products. Microbial material transformation products, i.e. organic compounds which can be obtained in this way, here comprise, for example, low molecular weight volatile compounds such as ethanol, nonvolatile material transformation products such as amino acids, vitamins and carotenoids and also many further materials. Volatile and nonvolatile microbial material transformation products having at least two carbon atoms can be prepared by fermentation by means of the process of the invention. Glucose obtainable by the process of the invention, which, as mentioned above, can comprise small amounts of oligosaccharides, is suitable for use here.

Microbial material transformation products which can be obtained by the process of the invention are, in particular, alcohols, e.g. ethanol, n-propanol, n-butanol, etc.; diols, e.g. ethanediol, propanediol and butanediol; higher-functional alcohols having 3 or more, e.g. 3, 4, 5 or 6, OH groups, e.g. glycerol, sorbitol, mannitol, xylitol and arabinitol; relatively long-chain monocarboxylic, dicarboxylic and tricarboxylic acids which bear 1 or more, e.g. 1, 2, 3 or 4, hydroxyl groups and preferably having 2 to 10 carbon atoms, e.g. glycolic acid, tartaric acid, itaconic acid, succinic acid, propionic acid, lactic acid, 3-hydroxypropionic acid, fumaric acid, maleic acid, 2,5-furandicarboxylic acid, glutaric acid, levulinic acid, gluconic acid, aconitic acid and citric acid; amino acids, e.g. lysine, glutamic acid, methionine, phenylalanine, aspartic acid, tryptophan and threonine; purine and pyrimidine bases; nucleosides and nucleotides, e.g. nicotinamide-adenine dinucleotide (NAD) and adenosine 5'-monophosphate (AMP); lipids; saturated and unsaturated fatty acids having preferably from 10 to 22 carbon atoms, e.g. γ-linolenic acid; vitamins and provitamins, e.g. ascorbic acid, vitamin $B_6$, vitamin $B_{12}$ and riboflavin; proteins, e.g. enzymes such as amylases, pectinases, cellulases, esterases such as lipases, pancreases, proteases, xylanases and oxidoreductases such as laccase, catalase and peroxidase, glucanases, phytases; carotenoids, e.g. lycopene, β-carotene, astaxanthin, zeaxanthin and canthaxanthin; ketones having preferably from 3 to 10 carbon atoms and, if appropriate, one or more hydroxyl groups, e.g. acetone and acetoin; lactones, e.g. γ-butyrolactone, cyclodextrins, biopolymers, e.g. polyhydroxyacetate, polyesters, e.g. polylactide, polyisoprenoids, polyamides; and also precursors and derivatives of the abovementioned compounds. Further microbial material transformation products are described by Gutcho in Chemicals by Fermentation, Noyes Data Corporation (1973), ISBN: 0818805086.

In particular, the material transformation products produced are selected from among alkanols having from 2 to 10 carbon atoms, alkanediols having from 2 to 10 carbon atoms, enzymes, amino acids, vitamins, aliphatic monocarboxylic and dicarboxylic acids having from 2 to 10 carbon atoms, aliphatic hydroxycarboxylic acids having from 2 to 10 carbon atoms and ketones having from 2 to 10 carbon atoms.

Compounds prepared by fermentation are in each case obtained in the enantiomeric form (if different enantiomers exist) produced by the microorganisms used. The microorganisms used in the fermentation depend in a manner known per se on the respective microbial material transformation products. They can be of natural origin or be genetically modified. Examples of suitable microorganisms and fermentation processes are given in table A.

TABLE A

| Material | Microorganism | Reference |
|---|---|---|
| Ethanol | *Saccharomyces, Schizosaccharomyces, Saccharomycodes, Torulopsis, Kluyveromyces, Zymomonas mobilis, E. coli* | The Alcohol Textbook - A reference for the beverage, fuel and industrial alcohol industries, Jaqus et al. (editors), Nottingham Univ. Press 1995, ISBN 1-8977676-735 |
| Tartaric acid | *Lactobacilli*, (e.g. *Lactobacillus delbrueckii*) | Rehm, H.-J.: Biotechnology, Weinheim, VCH, 1980 and 1993-1995; Gutcho, Chemicals by Fermentation, Noyes Data Corporation (1973), |
| Itaconic acid | *Aspergillus terreus, Aspergillus itaconicus* | Jakubowska, in Smith & Pateman (editors), Genetics and Physiology of *Aspergillus*, London: Academic Press 1977; Miall, in Rose (editors), Economic Microbiology, Vol. 2, p. 47-119, London: Academic Press 1978; U.S. Pat. No. 3,044,941 (1962). |
| Succinic acid | *Actinobacillus* sp. 130Z, *Anaerobiospirillum succiniproducens, Actinobacillus succinogenes, E. coli* | Int. J. Syst. Bacteriol. 26, 498-504 (1976); EP 249773 (1987), inventors: Lemme & Datta; U.S. Pat. No. 5,504,004 (1996), inventors: Guettler, Jain & Soni; Arch. Microbiol. 167, 332-342 (1997); Guettler MV, Rumler D, Jain MK., *Actinobacillus succinogenes* sp. nov., a novel succinic-acid-producing strain from the bovine rumen. Int J Syst Bacteriol. 1999 Jan; 49 Pt 1: 207-16; U.S. Pat. No. 5,723,322, U.S. Pat. No. 5,573,931, U.S. Pat. No. 5,521,075, WO99/06532, U.S. Pat. No. 5,869,301, U.S. Pat. No. 5,770,435 |
| Hydroxypropionic acid | *Lactobacillus delbrückii, L. leichmannii* or *Sporolactobacillus inulinus* | ROMPP Online Version 2.2 |
| Propionic acid | *Propionibacterium,* e.g. *P. arabinosum,* | Rehm, H.-J.: Biotechnology, Weinheim, VCH, 1980 and 1993-1995; |

TABLE A-continued

| Material | Microorganism | Reference |
|---|---|---|
| | P. schermanii, P. freudenreichii, Clostridium propionicum, | Gutcho, Chemicals by Fermentation, Noyes Data Corporation (1973), |
| Diaminopimelic acid | Corynebacterium glutamicum | Rehm, H.-J.: Biotechnology, Weinheim, VCH, 1980 and 1993-1995; Gutcho, Chemicals by Fermentation, Noyes Data Corporation (1973), |
| Citric acid | Aspergillus niger, Aspergillus wentii | Crit. Rev. Biotechnol. 3, 331-373 (1986); Food Biotechnol. 7, 221-234 (1993); 10, 13-27 (1996). |
| Aconitic acid | Aspergillus niger, Aspergillus wentii | Crit. Rev. Biotechnol. 3, 331-373 (1986); Food Biotechnol. 7, 221-234 (1993); 10, 13-27 (1996).; Rehm, H.-J.: Biotechnology, Weinheim, VCH, 1980 and 1993-1995; |
| Malic acid | Aspergilli, e.g. Aspergillus flavus, A. niger, A. oryzae, Corynebacterium | U.S. Pat. No. 3,063,910 |
| Gluconic acid | Aspergilli, e.g. A. niger | Gutcho, Chemicals by Fermentation, Noyes Data Corporation (1973), |
| Butyric acid | Clostridium (e.g. Clostridium acetobutylicum, C. butyricum) | Rehm, H.-J.: Biotechnology, Weinheim, VCH, 1980 and 1993-1995; |
| Lactic acid | Lactobacillus e.g. L. delbrückii, L. leichmannii, | Rehm, H.-J.: Biotechnology, Weinheim, VCH, 1980 and 1993-1995; |
| Lysine | Corynebacterium glutamicum | Ikeda, M.: Amino Acid Production Process (2003), Adv. Biochem. Engin/Biotechnol 79, 1-35. |
| Glutamic acid | Corynebacterium glutamicum | Ikeda, M.: Amino Acid Production Process (2003), Adv. Biochem. Engin/Biotechnol 79, 1-35. |
| Methionine | Corynebacterium glutamicum | Ikeda, M.: Amino Acid Production Process (2003), Adv. Biochem. Engin/Biotechnol 79, 1-35. |
| Phenylalanine | Corynebacterium glutamicum, E. coli | Trends Biotechnol. 3, 64-68 (1985); J. Ferment. Bioeng. 70, 253-260 (1990). |
| Threonine | E. coli | Ikeda, M.: Amino Acid Production Process (2003), Adv. Biochem. Engin/Biotechnol 79, 1-35. |
| Aspartic acid | E. coli | Ikeda, M.: Amino Acid Production Process (2003), Adv. Biochem. Engin/Biotechnol 79, 1-35 + refs. cited there, Gutcho, Chemicals by Fermentation, Noyes Data Corporation (1973) |
| Purine and pyrimidine bases | Bacillus subtilis | Rehm, H.-J.: Biotechnology, Weinheim, VCH, 1980 and 1993-1995; Gutcho, Chemicals by Fermentation, Noyes Data Corporation (1973), |
| Nicotinamide-adenine dinucleotide (NAD) | Bacillus subtilis | Rehm, H.-J.: Biotechnology, Weinheim, VCH, 1980 and 1993-1995; Gutcho, Chemicals by Fermentation, Noyes Data Corporation (1973), |
| Adenosine 5'-mono-phosphate (AMP) | Bacillus subtilis | Rehm, H.-J.: Biotechnology, Weinheim, VCH, 1980 and 1993-1995; Gutcho, Chemicals by Fermentation, Noyes Data Corporation (1973), |
| γ-Linolenic acid | Mucor, Mortiella, Aspergillus spp. | Gill, I., Rao, V.: Polyunsaturated fatty acids, part 1: occurrence, biological activities and applications (1997). Trends in Biotechnology 15 (10), 401-409; Zhu, H.: Utilization of Rice Bran by Pythium irregulare for Lipid Production. Master Thesis Louisiana State University, 31.10.2002 (URN etd-1111102-205855). |
| Dihomo-γ-linolenic acid | Mortiella, Conidiobolus, Saprolegnia spp. | Gill, I., Rao, V.: Polyunsaturated fatty acids, part 1: occurrence, biological activities and applications (1997). Trends in Biotechnology 15 (10), 401-409; Zhu, H.: Utilization of Rice Bran by Pythium irregulare for Lipid Production. Master Thesis Louisiana State University, 31.10.2002 (URN etd-1111102-205855). |
| Arachidonic acid | Mortiella, Phytium spp. | Gill, I., Rao, V.: Polyunsaturated fatty acids, part 1: occurrence, biological activities and |

TABLE A-continued

| Material | Microorganism | Reference |
|---|---|---|
| | | applications (1997). Trends in Biotechnology 15 (10), 401-409; Zhu, H.: Utilization of Rice Bran by *Pythium irregulare* for Lipid Production. Master Thesis Louisiana State University, 31.10.2002 (URN etd-1111102-205855). |
| Eicosapentaenic acid | *Mortiella, Phytium* spp., *Rhodopseudomonas, Shewanella* spp. | Gill, I., Rao, V.: Polyunsaturated fatty acids, part 1: occurrence, biological activities and applications (1997). Trends in Biotechnology 15 (10), 401-409; Zhu, H.: Utilization of Rice Bran by *Pythium irregulare* for Lipid Production. Master Thesis Louisiana State University, 31.10.2002 (URN etd-1111102-205855). |
| Docosahexaenic acid | *Thraustochytrium, Entomophthora* spp., *Rhodopseudomonas, Shewanella* spp. | Gill, I., Rao, V.: Polyunsaturated fatty acids, part 1: occurrence, biological activities and applications (1997). Trends in Biotechnology 15 (10), 401-409; Zhu, H.: Utilization of Rice Bran by *Pythium irregulare* for Lipid Production. Master Thesis Louisiana State University, 31.10.2002 (URN etd-1111102-205855). |
| Propanediol | *E. coli* | DE 3924423, U.S. Pat. No. 440379, WO 9635799, U.S. Pat. No. 5,164,309 |
| Butanediol | *Enterobacter aerogenes, Bacillus subtilis, Klebsiella oxytoca* | Rehm, H.-J.: Biotechnology, Weinheim, VCH, 1980 and 1993-1995; Gutcho, Chemicals by Fermentation, Noyes Data Corporation (1973); H. G. SCHLEGEL and H. W. JANNASCH, 1981; Afschar et al.: Mikrobielle Produktion von 2,3-butanediol. CIT 64 (6), 2004, 570-571 |
| Butanol | *Clostridium* (e.g. *Clostridium acetobutylicum, C. propionicum*) | Rehm, H.-J.: Biotechnology, Weinheim, VCH, 1980 and 1993-1995; Gutcho, Chemicals by Fermentation, Noyes Data Corporation (1973), |
| Glycerol | Yeast, *Saccharomyces rouxii* | Gutcho, Chemicals by Fermentation, Noyes Data Corporation (1973), |
| Mannitol | *Aspergillus candida, Torulopsis mannitofaciens* | Gutcho, Chemicals by Fermentation, Noyes Data Corporation (1973), |
| Arabitol | *Saccharomyces rouxii, S. mellis, Sclerotium glucanicum, Pichia ohmeri* | Gutcho, Chemicals by Fermentation, Noyes Data Corporation (1973), |
| Xylitol | *Saccharomyces cerevisiae* | Gutcho, Chemicals by Fermentation, Noyes Data Corporation (1973), |
| Hyaluronic acid | *Streptococcus* sp. | Rehm, H.-J.: Biotechnology, Weinheim, VCH, 1980 and 1993-1995; |
| Ascorbic acid | *Gluconobacter melanogenes* | ROMPP Online Version 2.2 |
| Vitamin $B_{12}$ | *Propionibacterium* spp., *Pseudomonas denitrificans* | Chem. Ber. 1994, 923-927; ROMPP Online Version 2.2 |
| Riboflavin | *Bacillus subtilis, Ashbya gossypii* | WO 01/011052, DE 19840709, WO 98/29539, EP 1186664; Fujioka, K.: New biotechnology for riboflavin (vitamin $B_2$) and character of this riboflavin. Fragrance Journal (2003), 31(3), 44-48. |
| Vitamin $B_6$ | *Rhizobium tropici, R. meliloti* | EP 0765939 |
| Enzymes | *Apergilli* (e.g. *Aspergillus niger A. oryzae*), *Trichoderma, E. coli, Hansenulna* or *Pichia* (e.g. *Pichia pastorius*), *Bacillus* (e.g. *Bacillus licheniformis, B. subtilis*) and many others. | Rehm, H.-J.: Biotechnology, Weinheim, VCH, 1980 and 1993-1995; Gutcho, Chemicals by Fermentation, Noyes Data Corporation (1973), |
| Zeaxanthin Canthaxanthin | *Dunaliella salina Brevibacterium* | Jin et al (2003) Biotech. Bioeng. 81: 115-124 Nelis et al (1991) J Appl Bacteriol 70: 181-191 |
| Lycopene | *Blakeslea trispora, Candida utilis* | WO 03/056028, EP 01/201762, WO 01/12832, WO 00/77234, Miura et al (1998) Appl Environ Microbiol 64: 1226-1229 |

TABLE A-continued

| Material | Microorganism | Reference |
|---|---|---|
| β-Carotene | *Blakeslea trispora*, *Candida utilis* | Kim S., Seo W., Park Y., Enhanced production of beta-carotene from *Blakeslea trispora* with Span 20, Biotechnology Letters, Vol 19, No 6, 1997, 561-562; Mantouridou F., Roukas T.: Effect of the aeration rate and agitation speed on beta-carotene production and morphology of *Blakeslea trispora* in a stirred tank reactor: mathematical modelling, Biochemical Engineering Journal 10 (2002), 123-135; WO 93/20183; WO 98/03480, Miura et al (1998) Appl Environ Microbiol 64: 1226-1229 |
| Astaxanthin | *Phaffia Rhodozyma*; *Candida utilis* | U.S. Pat. No. 5,599,711; WO 91/02060, Miura et al (1998) Appl Environ Microbiol 64: 1226-1229 |
| Polyhydroxy-alkanoates, Polyesters | *Escherchia coli*, *Alcaligenes latus*, and many others. | S. Y. Lee, Plastic Bacteria Progress and Prospects for polyhydroxyalkanoate production in bacteria, Tibtech, Vol. 14, (1996), p. 431-438., Steinbüchel, 2003; Steinbüchel (editor), Biopolymers, 1st edition, 2003, Wiley-VCH, Weinheim and references cited there |
| Polyisoprenoids | *Lactarius* sp., *Hygrophorus* sp., *Russula* sp. | Steinbüchel (editor), Biopolymers, 1st edition, 2003, Wiley-VCH, Weinheim and references cited there |
| Acetone | *Clostridium* (e.g. *Clostridium acetobutylicum*, *C. propionicum*) | Rehm, H.-J.: Biotechnology, Weinheim, VCH, 1980 and 1993-1995; Gutcho, Chemicals by Fermentation, Noyes Data Corporation (1973) |
| Acetoin | *Enterobacter aerogenes*, *Clostridium acetobutylicum*, *Lactococcus lactis* | Lengeler, J. W., Drews, G., Schlegel, H. G.: editors., Biology of the Procaryotes, Thieme, Stuttgart (1999), p.307; ROMPP Online-Edition |
| Thurigensin | *Bacillus thuringiensis* | Jian-Zhong Jong et al.: Fed-batch culture of *Bacillus thuringiensis* for thuringensin production in a tower type bioreactor. Biotechnology and Bioengineering 48 (3) (2004), 207-213. |
| Polyketides | *Streptomyces fradiae*, *Sorangium cellulosum* | Kirst: Fermentation-derived compounds as a source for new products. Pure & Appl. Chem. 70 (2), (1998), 335-338; Zirkle et al.: Heterologous production of the antifungal polyketide antibiotic soraphen A of *Sorangium cellulosum* So ce26 in Streptomyces lividans. Microbiology 150 (8), (2004), 2761-74. |
| Gibberellic acid | *Gibberella fujikuroi* | Hollmann et al.: Extraktiv-Fermentation von Gibberellinsäure mit Gibberella fujikuroi. CIT 7 (1995), 892-895. |

In a preferred embodiment, the fermentation is carried out without addition of separate enzymes.

In the process of the invention for preparing a microbial material transformation product, it is also possible to use immobilized microorganisms. To immobilize the microorganisms, they are, for example, mixed with a support protein (e.g. gelatin) and crosslinked by means of glutaraldehyde and embedded in a synthetic polymer, e.g. polyacrylamide, or in a natural polymer such as agar, collagen, kappa-carrageenin or alginate. Suitable fermentation vessels are in principle vessels configured in the manner of a bioreactor and are known to those skilled in the art.

In preferred embodiments of the invention, the organic compound prepared is ethanol. The fermentation in step h) for the preparation of ethanol can be carried out using the appropriate microorganisms shown in table A), e.g. as anaerobic fermentation (alcoholic fermentation). To isolate the ethanol, it is advantageous firstly to remove the solid constituents from the fermentation broth, e.g. by means of centrifugation or filtration, and subsequently to isolate the ethanol from the liquid phase, e.g. by distillation. Customary filtration methods are, for example, cake filtration and deep bed filtration (e.g. described in A. Rushton, A. S. Ward, R. G. Holdich: Solid-Liquid Filtration and Separation Technology, VCH Verlagsgesellschaft, Weinheim 1996, pp. 177ff., K. J. Ives, in A. Rushton (editor): Mathematical Models and Design Methods in Solid-Liquid Separation, NATO ASI series E No. 88, Martinus Nijhoff, Dordrecht 1985, pp. 90ff.) and cross-flow fitrations, in particular the microfiltration for the removal of solids >0.1 µm (described, for example, in J. Altmann, S. Ripperger, J. Membrane Sci. 124 (1997) 119-128.). Customary centrifugation methods are described, for example, in G. Hultsch, H. Wilkesmann, "Filtering Centrifuges," in D. B. Purchas, Solid-Liquid Separation, Upland Press, Croydon 1977, pp. 493-559; and H. Trawinski, Die äquivalente Klärfläche von Zentrifugen, Chem. Ztg. 83 (1959) 606-612. The alcohol present in the mash is distilled by methods customary in the prior art and, if appropriate, purified further. The known methods of distillation, rectification and dewatering can be used here.

The invention is illustrated by the following, nonlimiting examples.

The cellulose activity was determined by the standard filter paper assay and reported as filter paper units per gram of glucan (FPU) (chose Tk. 1987, Measurement of cellulase activities. Pure Appl. Chem. 59 (2):257-268).

I. Dissolution of Cellulose in and Regeneration from an Ionic Liquid 540 g of 1-ethyl-3-methylimidazolium acetate (prepared from 1-ethyl-3-methyl-1H-imidazolium chloride (e.g. commercially available from Sigma-Aldrich, Germany) by anion exchange with potassium acetate) were heated to 100° C. and 60 g of cellulose (Avicel® Ph-101, FMC (Philadelphia, USA), average degree of polymerization DP=460) were added a little at a time over a period of five minutes while stirring by means of a rod mixer. The cellulose became finely dispersed in the ionic liquid. Formation of lumps was not observed. The mixture was subsequently stirred by means of a serrated blade stirrer for a further 30 minutes, resulting in the cellulose dissolving completely. 1.5 l of hot water were added to this solution, resulting in the cellulose precipitating as flocs. A further 0.9 l of hot water was subsequently added and the mixture was stirred for a further 60 minutes. The precipitate obtained was filtered off with suction, admixed with 1.5 l of water and the mixture was boiled for 1 hour. The precipitate was filtered off with suction and washed three times with 250 ml each time of hot water. Yield of cellulose: 484 g. To recover the ionic liquid, the filtrate was evaporated at 80° C. and 2 mbar until the water content was about 10%. The ionic liquid (yield about 92%) was then used in a subsequent experiment, as was the washing water which still comprised about 7% of ionic liquid.

A sample of the regenerated cellulose was dried overnight at 90° C. and 20 mbar in a drying oven. The dry mass content was 11.9%, so that a yield of cellulose of about 96% resulted.

Determination of the degree of polymerization by means of viscometry:

The determination was carried out by the "Cuen method" in accordance with DIN 54270. The average degree of polymerization DP was 448.

II. Enzymatic Degradation of Cellulose which has been Pretreated with Ionic Liquid Cellulose (average degree of polymerization=448) obtainable as described above in I was suspended in a concentration of 4% in 0.05 M aqueous acetate buffer. The cellulase mixture Celluclast 1.5 L (with Novozym 188 from Novozymes, Denmark, in a volvmetric ratio of 1:4) was added thereto in an amount of 28 FPU/g of cellulose. The mixture was incubated at 55° C., pH 4.8, for 48 hours.

Figure 3:
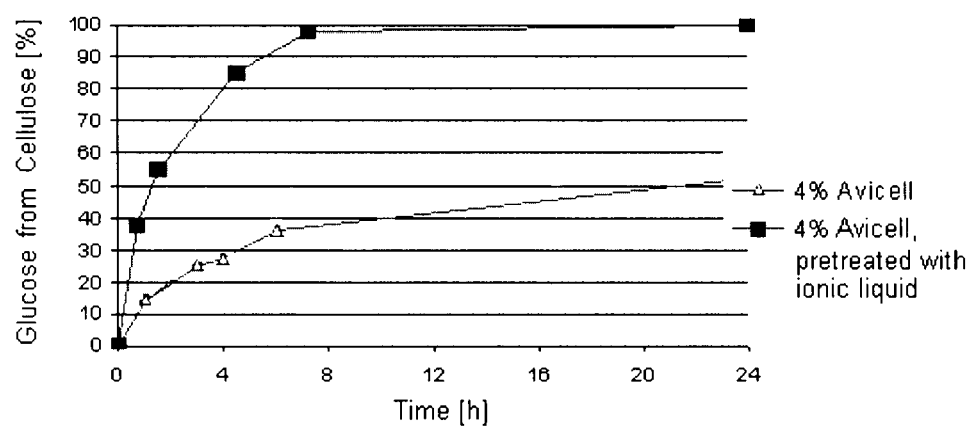

After taking a sample, it was briefly heated to 99° C. to deactivate the enzyme. The results are shown graphically in FIG. 3.

As can be seen from the figure, the liberation rate of glucose in the case of cellulose pretreated with an ionic liquid is significantly increased compared to cellulose which has not been pretreated. The insoluble, solid cellulose is degraded to form soluble glucose monomers having a DP of 1 within 8 hours. Without pretreatment with an ionic liquid, only 40% of the cellulose is degraded to glucose after 8 hours.

The invention claimed is:

1. A process for preparing glucose from a cellulose material, wherein
a cellulose-comprising starting material is provided and is treated with a liquid treatment medium comprising at least one ionic liquid whose anions are polyatomic anions and
the cellulose-comprising material which has been treated with the ionic liquid is subjected to an enzymatic hydrolysis.

2. The process according to claim 1, wherein said cellulose material is selected from the group consisting of wood fibers, linters, pulp, cotton, cellulose obtained from paper, regenerated cellulose and bacterial cellulose.

3. The process according to claim 1, wherein the cellulose-comprising starting material is at least one cellulose-rich natural fiber materials selected from the group consisting of flax, hemp, sisal, jute, straw, coconut fibers, switchgrass (*Panicum virgatum*) and other natural fibers.

4. The process according to claim 1, wherein the at least one ionic liquid is at least one member selected from the group consisting of (A) salts of general formula (I)

where n is 1, 2, 3 or 4, $[A]^+$ is a quaternary ammonium cation, an oxonium cation, a sulfonium cation or a phosphonium cation and $[Y]^-$ is a multiatomic, monovalent, divalent, trivalent or tetravalent anion or a mixture of these anions;

(B) mixed salts of general formulae (II.a), (II.b) or (II.c)

 (II.a), where n=2,

 (II.b), where n=3,

 (II.c), where n=4, where $[A^1]^+$, $[A^2]^+$, $[A^3]^+$ and $[A^4]^+$ are selected independently from among the groups mentioned for $[A]^+$ and $[Y]^{n-}$ is as defined under (A); and (C) mixed salts of general formulae (III.a) to (III.j)

 (III.a), where n=4,

 (III.b), where n=4,

 (III.c), where n=4,

 (III.d), where n=3,

 (III.e), where m=3,

 (III.f), where n=2,

 (III.g), where n=4,

 (III.h), where n=4,

 (III.i), where n=4,

 (III.j), where n=3, where $[A^1]^+$, $[A^2]^+$ and $[A^3]^+$ are selected independently from among the groups mentioned for $[A]^+$, $[Y]^{n-}$ is as defined under (A) and $[M^1]^+$, $[M^2]^+$, $[M^3]^+$ are monovalent metal cations, $[M^4]^{2+}$ are divalent metal cations and $[M^5]^{3+}$ are trivalent metal cations.

5. The process according to claim 1, wherein the at least one ionic liquid has at least one cation of represented by formulae (IV.a) to (IV.z),

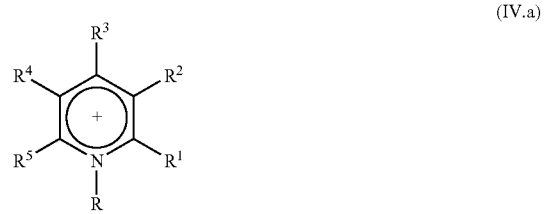

(IV.a)

-continued
(IV.b)
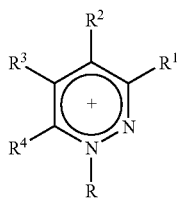
(IV.c)
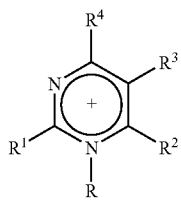
(IV.d)
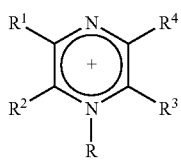
(IV.e)
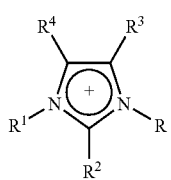
(IV.f)
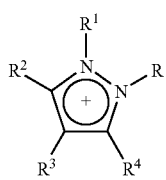
(IV.g)
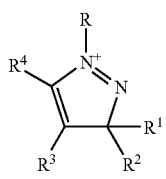
(IV.g')
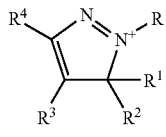
(IV.h)
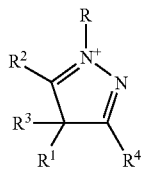
(IV.i)
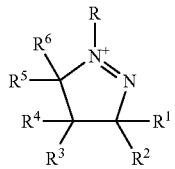
-continued
(IV.j)
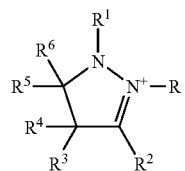
(IV.j')
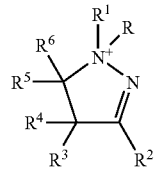
(IV.k)
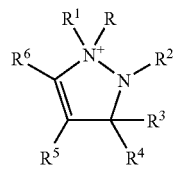
(IV.k')
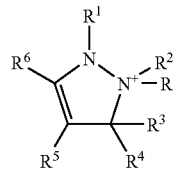
(IV.l)
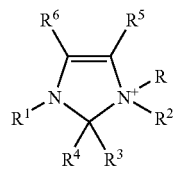
(IV.m)
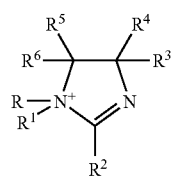
(IV.m')
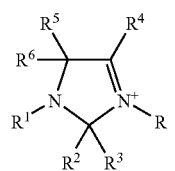
(IV.n)
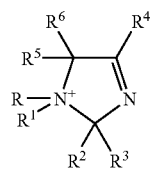
(IV.n')

-continued

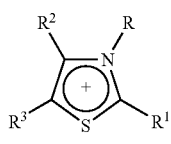 (IV.o)

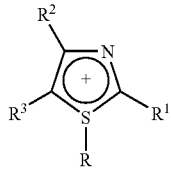 (IV.o′)

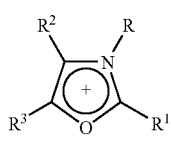 (IV.p)

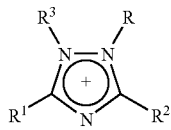 (IV.q)

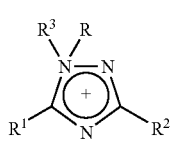 (IV.q′)

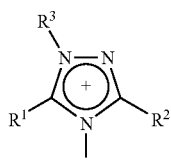 (IV.q″)

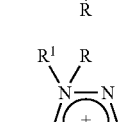 (IV.r)

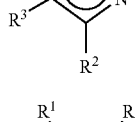 (IV.r′)

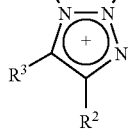 (IV.r″)

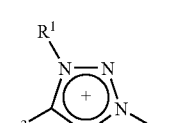 (IV.s)

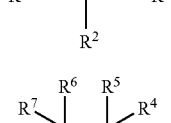

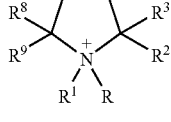

-continued

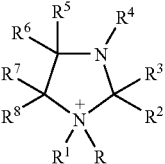 (IV.t)

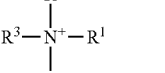 (IV.u)

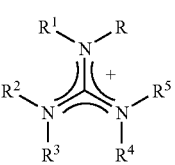 (IV.v)

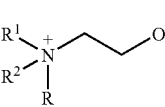 (IV.w)

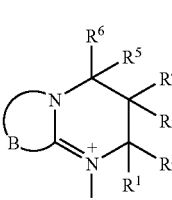 (IV.x.1)

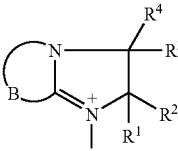 (IV.x.2)

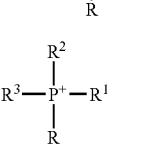 (IV.y)

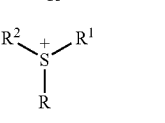 (IV.z)

and oligomers comprising these structures, where
R is hydrogen, alkyl, alkenyl, cycloalkyl, cycloalkenyl, polycyclyl, heterocycloalkyl, aryl or heteroaryl;
radicals $R^1$, $R^2$, $R^3$, $R^4$, $R^5$, $R^6$, $R^7$, $R^8$ and $R^9$ which are bound to a ring carbon are each, independently of one another, hydrogen, a sulfo group, COOH, carboxylate, sulfonate, acyl, alkoxycarbonyl, cyano, halogen, hydroxyl, SH, nitro, $NE^1E^2$, alkyl, alkoxy, alkylthio, alkylsulfinyl, alkylsulfonyl, alkenyl, cycloalkyl, cycloalkyloxy, cycloalkenyl, cycloalkenyloxy, polycyclyl, polycyclyloxy, heterocycloalkyl, aryl, aryloxy or heteroaryl, where $E^1$ and $E^2$ are each, independently of one another, hydrogen, alkyl, cycloalkyl, heterocycloalkyl, aryl or hetaryl,
radicals $R^1$, $R^2$, $R^3$, $R^4$, $R^5$, $R^6$, $R^7$, $R^8$ and $R^9$ which are bound to a ring heteroatom are each hydrogen, $SO_3H$, $NE^1E^2$, alkyl, alkoxy, alkenyl, cycloalkyl, cycloalkenyl, polycyclyl, heterocycloalkyl, aryl or heteroaryl, where $E^1$ and $E^2$ are each, independently of one another, hydrogen, alkyl, cycloalkyl, heterocycloalkyl, aryl or hetaryl, or two adjacent radicals $R^1$ to $R^9$ together with the ring atoms to which they are bound may also form at least one fused-on, saturated, unsaturated or aromatic ring or a ring system having from 1 to 30 carbon atoms, where the ring or the ring system may have from 1 to 5 nonadjacent heteroatoms or heteroatom-comprising groups and the ring or the ring system may be unsubstituted or substituted, two geminal radicals $R^1$ to $R^9$ may also together be $=O$, $=S$ or $=NR^b$, where $R^b$ is hydrogen, alkyl, cycloalkyl, aryl or heteroaryl, and $R^1$ and $R^3$ or $R^3$ and $R^5$ in the compounds of the formula (IV.x.1) may together also represent the second part of a double bond between the ring atoms bearing these radicals, and B in the compounds of the formulae (IV.x.1) and (IV.x.2), together with the C—N group to which it is bound, forms a 4- to 8-membered, saturated or unsaturated or aromatic ring.

6. The process according to claim 5, wherein the at least one ionic liquid has at least one cation represented by formula (IV.e).

7. The process according to claim 1, wherein the at least one ionic liquid has at least one anion of:
pseudohalides and halogen-comprising compounds of formulae:

$BF_4^-$, $PF_6^-$, $CF_3SO_3^-$, $(CF_3SO_3)_2N^-$, $CF_3CO_2^-$, $CCl_3CO_2^-$, $CN^-$, $SCN^-$, $OCN^-$;

sulfates, sulfites and sulfonates of formulae:

$SO_4^{2-}$, $HSO_4^-$, $SO_3^{2-}$, $HSO_3^-$, $R^cOSO_3^-$, $R^cSO_3^-$;

phosphates of formulae:

$PO_4^{3-}$, $HPO_4^{2-}$, $H_2PO_4^-$, $R^cPO_4^{2-}$, $HR^cPO_4^-$, $R^cR^dPO_4^-$;

phosphonates and phosphinates general formulae:

$R^cHPO_3^-$, $R^cR^dPO_2^-$, $R^cR^dPO_3^-$;

phosphites of formulae:

$PO_3^{3-}$, $HPO_3^{2-}$, $H_2PO_3^-$, $R^cPO_3^{2-}$, $R^cHPO_3^-$, $R^cR^dPO_3^-$;

phosphonites and phosphinites of formulae:

$R^cR^dPO_2^-$, $R^cHPO_2^-$, $R^cR^dPO^-$, $R^cHPO^-$;

carboxylic acids of formula:

$R^cCOO^-$;

anions of hydroxycarboxylic acids and sugar acids; saccharinates
borates of formulae:

$BO_3^{3-}$, $HBO_3^{2-}$, $H_2BO_3^-$, $R^cR^dBO_3^-$, $R^cHBO_3^-$, $R^cBO_3^{2-}$, $B(OR^c)(OR^d)(OR^e)(OR^f)^-$, $B(HSO_4)_4^-$, $B(R^cSO_4)_4^-$;

boronates of formulae:

$R^cBO_2^{2-}$, $R^cR^dBO^-$;

carbonates and carboxylic esters of formulae:

$HCO_3^-$, $CO_3^{2-}$, $R^cCO_3^-$;

silicates and silicic esters of formulae:

$SiO_4^{4-}$, $HSiO_4^{3-}$, $H_2SiO_4^{2-}$, $H_3SiO_4^-$, $R^cSiO_4^{3-}$, $R^cR^dSiO_4^{3-}$, $R^cR^dR^eSiO_4^-$, $HR^cSiO_4^{2-}$, $H_2R^cSiO_4^-$, $HR^cR^dSiO_4^-$;

alkylsilanolates and arylsilanolates of formulae:

$R^cSiO_3^{3-}$, $R^cR^dSiO_2^{2-}$, $R^cR^dR^eSiO^-$, $R^cR^dR^eSiO_2^-$, $R^cR^dSiO_3^{2-}$;

carboximides, bis(sulfonyl)imides and sulfonylimides of formulae:

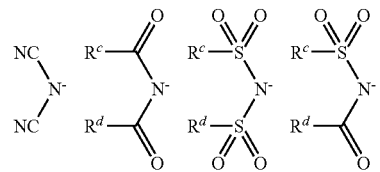

methides of formula:

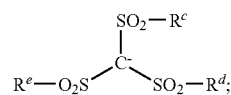

alkoxides and aryloxides of formula $R^c O^-$;
hydrogensulfides, polysulfides, hydrogenpolysulfides and thiolates of formulae:

$HS^-$, $[S_v]^{2-}$, $[HS_v]^-$, $[R^cS]^-$, where v is a positive integer from 2 to 10, where the radicals $R^c$, $R^d$, $R^e$ and $R^f$ are each independently hydrogen, alkyl, cycloalkyl, heterocycloalkyl, aryl, heteroaryl, and in anions which have a plurality of radicals $R^c$ to $R^f$, two of these radicals together with the part of the anion to which they are bound can also form at least one saturated, unsaturated or aromatic ring or a ring system having from 1 to 12 carbon atoms, where the ring or the ring system can have from 1 to 5 nonadjacent heteroatoms or heteroatom-comprising groups which are selected from the group consisting of oxygen, nitrogen, sulfur and $NR^a$ and the ring or the ring system is unsubstituted or may be substituted.

8. The process according to claim 1, wherein the at least one ionic liquid has at least one anion selected from the group consisting of pseudohalides, and halogen-comprising compounds, carboxylic acids, sulfates, sulfites and sulfonates and phosphates.

9. The process according to claim 1, wherein the water content of the liquid treatment medium is from 0.1 to 15% by weight, based on the weight of the total treatment liquid.

10. The process according to claim 1, wherein the cellulose-comprising starting material is dissolved in the liquid treatment medium.

11. The process according to claim 10, wherein the cellulose is precipitated after the treatment by addition of a precipitant.

12. The process according to claim 11, wherein the precipitant is selected from the group consisting of water, water-miscible organic solvents and mixtures thereof.

13. The process according to claim 12, wherein a water-comprising medium is present as precipitant.

14. The process according to claim 12, wherein an organic solvent is present as precipitant.

15. The process according to claim 11, wherein the mixture obtained in the precipitation is separated into a fraction comprising the precipitated cellulose and a liquid discharge (A1).

16. The process according to claim 15, wherein the discharge (A1) is subjected to a separation into a fraction (IL1) comprising the ionic liquid and a fraction (F1) comprising the precipitant.

17. The process according to claim 16, wherein the fraction (IL1) comprising essentially the ionic liquid is recycled for treatment of the cellulose-comprising starting material.

18. The process according to claim 1, wherein the precipitated cellulose is subjected to a treatment to remove ionic liquid still comprised.

19. The process according to claim 18, wherein the precipitated cellulose is subjected to washing with a liquid washing medium.

20. The process according to claim 19, wherein the treatment of the cellulose with a washing medium is carried out at a temperature of at least 40° C.

21. The process according to claim 19, wherein the washing medium comprises water.

22. A process for preparing glucose from a cellulose material and then preparing a microbial material transformation product having at least two carbon atoms, which comprises
providing and treating a cellulose-comprising starting material with a liquid treatment medium comprising at least one ionic liquid whose anions are polyatomic anions;
subjecting the cellulose-comprising material which has been treated with the ionic liquid to an enzymatic hydrolysis to obtain glucose; and fermenting the glucose.

23. The process according to claim 22, wherein the material transformation product comprises ethanol.

24. The process according to claim 1, which comprises:
a) treatment of the cellulose-comprising starting material with a liquid treatment medium comprising an ionic liquid to give a solution of cellulose in the treatment medium,
b) precipitation of the cellulose from the solution obtained in a) by addition of a precipitant,
c) separation into a fraction comprising the precipitated cellulose and a first liquid discharge (A1),
d) separation of the discharge (A1) into a fraction (IL1) comprising the ionic liquid and a fraction (F1) comprising the precipitant, with the fraction (IL1) comprising the ionic liquid being at least partly recirculated to a),
e) treatment of the precipitated cellulose with a liquid washing medium to remove ionic liquid still comprised, with the washing medium comprising the fraction (F1) comprising the precipitant which is obtained in d),
f) separation into a fraction comprising the precipitated, purified cellulose and a second liquid discharge (A2) which is at least partly recirculated as precipitant to b),
g) use of the cellulose obtained in step f) in the enzymatic hydrolysis.

25. The process according to claim 24, wherein a water-comprising medium, is present as precipitant in b) and as washing medium in e).

26. The process according to claim 25, wherein the treatment with the water-comprising medium in e) is carried out at a temperature of at least 80° C.

27. The process according to claim 1, which comprises:
a) treatment of the cellulose-comprising starting material with a liquid treatment medium comprising an ionic liquid to give a solution of cellulose in the treatment medium,
b) precipitation of the cellulose from the solution obtained in a) by addition of a precipitant comprising at least one water-miscible organic solvent,
c) separation into a fraction comprising the precipitated cellulose and a first liquid discharge (A1),
d) separation of the discharge (A1) into a fraction (IL1) comprising essentially the ionic liquid and a fraction (F1) comprising essentially the precipitant, (IL1) being at least partly recirculated to a) and (F1) being at least partly recirculated to b),
e) treatment of the precipitated cellulose with a liquid washing medium to remove ionic liquid still comprised,
f1) separation into a fraction comprising the precipitated, purified cellulose and a second liquid discharge (A2),
f2) separation of the discharge (A2) into
a fraction (IL2) which comprises the ionic liquid and is at least partly recirculated to a),
a fraction (F2) which comprises the precipitant and is at least partly recirculated to b),
a water-comprising fraction which is at least partly recirculated to e),
g) use of the cellulose obtained in step f2) in the enzymatic hydrolysis.

28. A process for preparing glucose from a cellulose material and then preparing at least one microbial material transformation product having at least two carbon atoms,
a) treatment of the cellulose-comprising starting material with a liquid treatment medium comprising an ionic liquid to give a solution of cellulose in the treatment medium,
b) precipitation of the cellulose from the solution obtained in a) by addition of a precipitant,
c) separation into a fraction comprising the precipitated cellulose and a first liquid discharge (A1),
d) separation of the discharge (A1) into a fraction (IL1) comprising the ionic liquid and a fraction (F1) comprising the precipitant, with the fraction (IL1) comprising the ionic liquid being at least partly recirculated to a),
e) treatment of the precipitated cellulose with a liquid washing medium to remove ionic liquid still comprised, with the washing medium comprising the fraction (F1) comprising the precipitant which is obtained in d),
f) separation into a fraction comprising the precipitated, purified cellulose and a second liquid discharge (A2) which is at least partly recirculated as precipitant to b),
g) subjecting the cellulose of (f) to enzymatic hydrolysis to obtain glucose; and
h) fermentation of the glucose obtained in g).

29. The process according to claim 28, wherein ethanol is obtained as microbial material transformation product in h).

30. The process according to claim 1, wherein the water content of the liquid treatment medium is from 0.5 to 10% by weight, based on the weight of the total treatment liquid.

31. The process according to claim 1, wherein the water content of the liquid treatment medium is from 1 to 8% by weight, based on the weight of the total treatment liquid.

32. The process according to claim 19, wherein the treatment of the cellulose with a washing medium is carried out at a temperature of at least 60° C.

33. The process according to claim 19, wherein the treatment of the cellulose with a washing medium is carried out at a temperature of at least 80° C.

34. The process according to claim 15, wherein the discharge (A1) is subjected to a separation into a fraction (IL1) consisting essentially of the ionic liquid and a fraction (F1) consisting essentially of the precipitant.

35. The process according to claim 24, wherein water is present as precipitant in b) and as washing medium in e).

36. The process according to claim 25, wherein the treatment with the water-comprising medium in e) is carried out at a temperature of at least 90° C.

37. The process according to claim 25, wherein the treatment with the water-comprising medium in e) is carried out at a temperature of at least 95° C.

38. The process according to claim 19, wherein the washing medium consists of water.

39. The process according to claim 5, wherein
B in the compounds of the formulae (IV.x.1) and (IV.x.2), together with the C—N group to which it is bound, forms a 4- to 8-membered, saturated or unsaturated or aromatic ring which has at least one of a subsituent; a further heteroatom within the ring; a group containing a heteroatom; a fused-on, a saturated, an unsaturated, or an aromatic carbocycle; and a fused-on, a saturated, an unsaturated, or an aromatic heterocycle.

40. A process for preparing glucose from a cellulose material, comprising
treating a cellulosic starting material with a liquid medium comprising at least one ionic liquid; and
hydrolyzing the cellulosic material obtained from said treating in the presence of at least one enzyme, wherein the anion of the at least one ionic liquid is a polyatomic anion.

* * * * *